United States Patent [19]

Singh

[11] Patent Number: 5,624,928
[45] Date of Patent: Apr. 29, 1997

[54] METHOD OF SYNTHESIZING AN ENDONUCLEASE INHIBITOR AND ANALOGS THEREOF

[75] Inventor: Sheo B. Singh, Edison, N.J.

[73] Assignee: Merck & Co., Inc., Rahway, N.J.

[21] Appl. No.: 324,557

[22] Filed: Oct. 18, 1994

[51] Int. Cl.⁶ ........................ A61K 31/495; C07D 241/18
[52] U.S. Cl. ............................ 514/255; 544/383; 560/39; 548/542
[58] Field of Search ............................. 544/383; 514/255

[56] References Cited

FOREIGN PATENT DOCUMENTS 2314091  10/1973  Germany ............................. 544/383
2280435  2/1995  United Kingdom .

OTHER PUBLICATIONS

Goetz et al, Chemical Abstracts, vol. 122, No. 235152 (1995) (Abstract for GB 2,280,435, Feb. 1, 1995).
Hensens et al, Tetrahedron Letters 36, pp. 2005–2008 (1995).
Singh, Tetrahedron Letters, 36, pp. 2009–2012 (1995).
Drug Evaluations Annual 1993 by American Medical Association, pp. 1723–1724, 1735–1736, (1993).

Primary Examiner—Emily Bernhardt
Attorney, Agent, or Firm—Elliott Korsen; Mark R. Daniel

[57] ABSTRACT

There is disclosed a method of synthesizing a compound of the formula

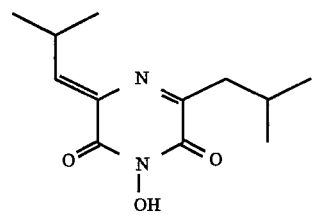
(I)

and novel analogs of the formula

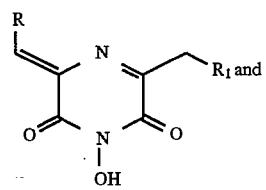
(II)

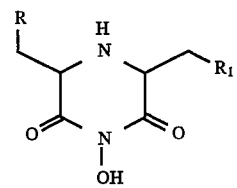

(III)

where R and $R_1$ are fully defined.

These compounds exhibit beneficial antiviral properties especially as inhibitors of the influenza virus.

6 Claims, No Drawings

METHOD OF SYNTHESIZING AN ENDONUCLEASE INHIBITOR AND ANALOGS THEREOF

SUMMARY OF THE INVENTION

The present invention relates to a method of synthesizing a compound having antiviral properties and analogs thereof.

The present invention also relates to compounds which exhibit antiviral properties, in particular as endonuclease transcription inhibitors against the influenza virus.

The compound disclosed in copending application Ser. No. 08/099,087, has been found to inhibit the transcription apparatus of the influenza virus which is required to initiate viral mRNA (messenger RNA) synthesis. This property renders the compound useful for the treatment and/or prevention of influenza.

Additionally, the invention is directed to a method for inhibiting the functioning of the transcription apparatus of influenza virus in the host cell. Thus, the present invention is further directed to a method of inhibiting the influenza endonucleolytic cleavage of host cell mRNA, a required step for the initiation of cap dependent influenza transcription, by administering a prophylactic or therapeutic amount of the compounds of the invention.

DETAILED DESCRIPTION OF THE INVENTION

This invention is directed to a novel method of synthesizing the natural compound of the formula (I)

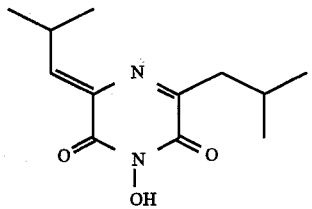

which comprises cyclizing a compound of the formula

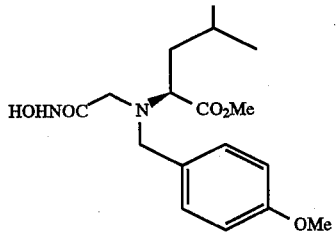

to afford a compound of the formula

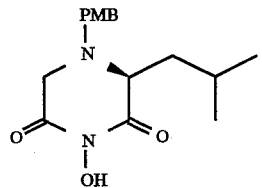

protecting the N-hydroxy group of said compound with a suitable protecting group selected from methoxymethyl chloride or tert-butyldimethylsilyl to afford a compound of the formula

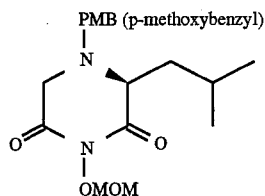

reacting said protected compound with dichlorodicyanoquinone or other suitable oxidizing agents to afford the compound of the formula

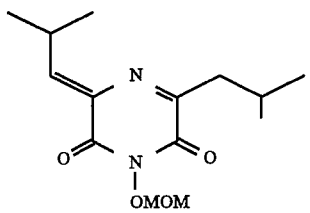

and deprotecting the N-hydroxy group by reacting with trifluoroacetic acid, described in copending application 08/099,087. This method also enables the synthesis of analogs of the natural compound not found in nature.

These analogs include compounds of the formula (II)

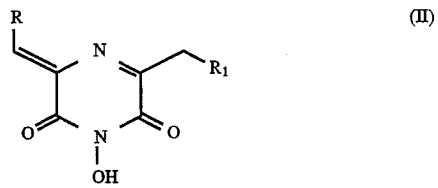

wherein:
R is $C_1$–$C_6$ alkyl, aryl, substituted aryl wherein the substituents are selected from halogen, $C_1$–$C_6$ alkoxy or aryloxy;

$R_1$ is $C_1$–$C_6$ alkyl, aryl, substituted aryl wherein the substituents are selected from halogen, $C_1$–$C_6$ alkoxy or aryloxy;

or a pharmaceutically acceptable salt thereof, or where applicable, a geometrical isomer or racemic mixture thereof.

Additionally, they include tetrahydro compounds of the formula (III)

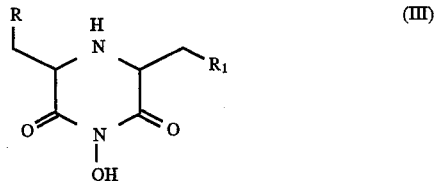

wherein
R is $C_1$–$C_6$ alkyl, aryl, substituted aryl wherein the substituents are selected from halogen, $C_1$–$C_6$ alkoxy or aryloxy;

$R_1$ is $C_1$–$C_6$ alkyl, aryl, substituted aryl wherein the substituents are selected from halogen, $C_1$–$C_6$ alkoxy or aryloxy;

or a pharmaceutically acceptable salt thereof, or, where applicable, a geometrical isomer or racemic mixture thereof.

Unless otherwise stated or indicated, the following definitions shall apply throughout the specification and appended claims.

The term alkyl refers to a monovalent straight or branched group having the predefined number of carbon atoms, e.g., methyl, ethyl, n-propyl, isopropyl, n-butyl, isobutyl, t-butyl and straight and branched chain pentyl and hexyl.

The term aryl refers to aromatic rings, e.g., phenyl, naphthyl, substituted phenyl and the like. The preferred group is phenyl.

The term halogen refers to F, Cl, Br or I.

Throughout the specification and appended claims, a given chemical formula or name shall encompass all geometrical isomers where such isomers exist.

In a preferred embodiment of this invention are compounds of formula (I) wherein:

R is $C_1$–$C_6$ alkyl or substituted aryl wherein the substituents are fluorine or $C_1$–$C_6$ alkoxy; and $R_1$ is $C_1$–$C_6$ alkyl or aryl.

As shown in the below synthetic schemes, the compound of formula (I) and analogs of formulas (II) and (III) can be prepared as follows:

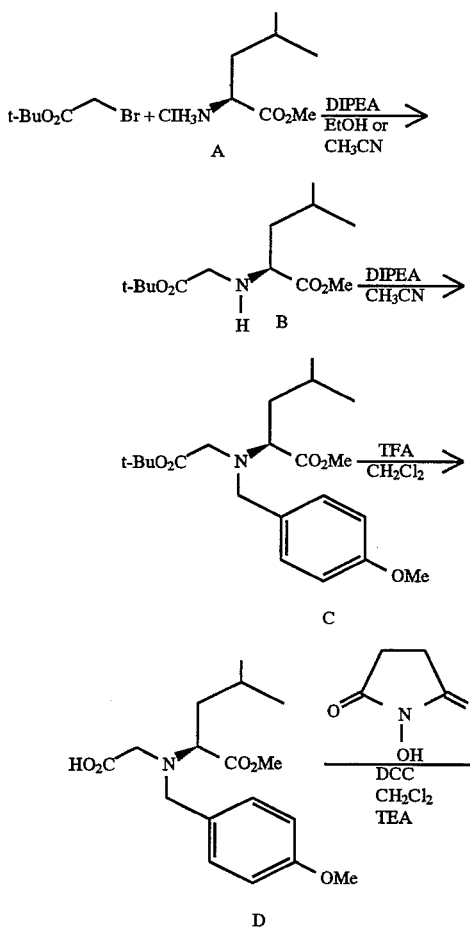

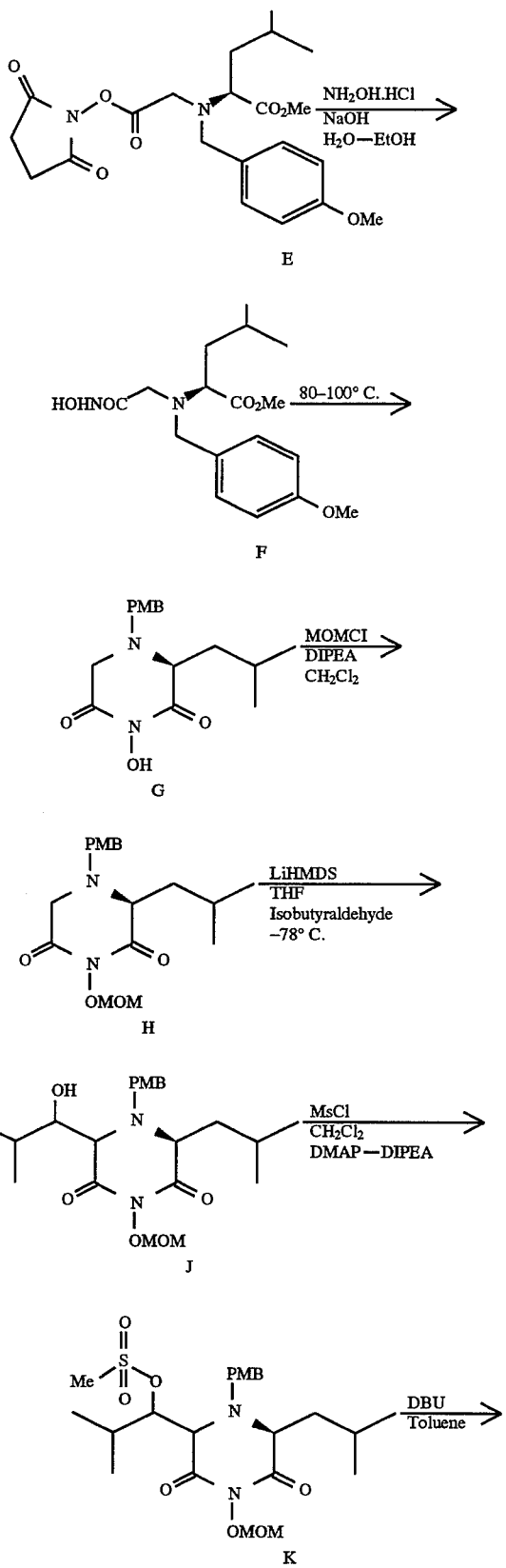

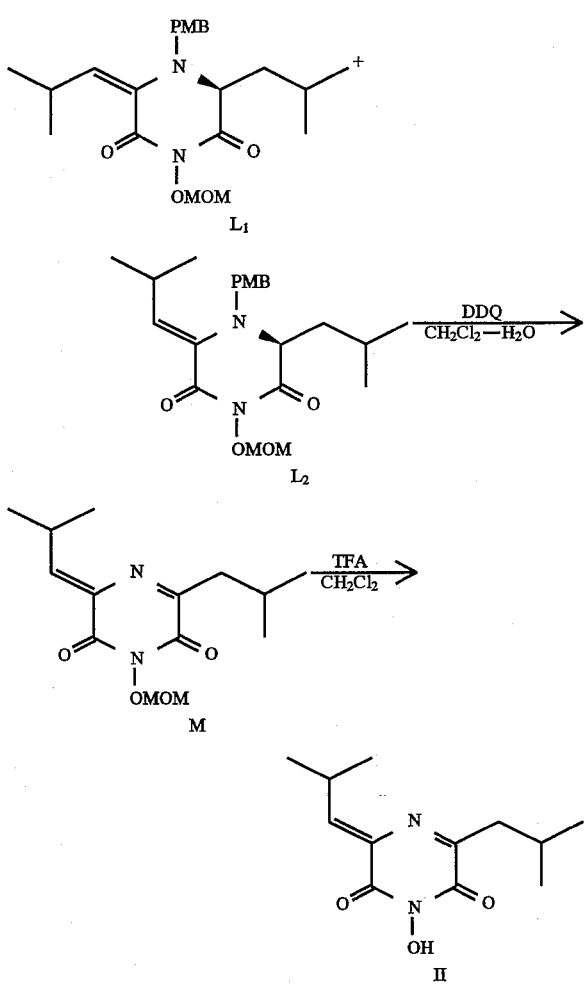

Leu-OME,HCl is alkylated with t-butyl bromomethyl acetate to afford Compound B. This reaction is typically conducted in the presence of a tertiary amine such as diisopropylethylamine and a suitable solvent such as ethanol, acetonitrile or the like at a temperature of about 25° C. to 80° C. for 10 to 20 hours.

Compound B is reacted with p-methoxybenzyl chloride to afford Compound C in good yield. Typically, this reaction is conducted in the presence of a suitable tertiary amine such as diisopropylethylamine and a nonalcoholic solvent such as acetonitrile or dimethylformamide at a temperature of about 60° C. to 100° C. for 15 to 30 hours.

Compound C is subsequently reacted with trifluoroacetic acid to cleave the t-butyl ester and afford Compound D. This reaction takes place in the presence of a suitable solvent such as dichloromethane at a temperature of about −78° C. to 25° C. for 10 to 70 hours.

Compound D is activated with N-hydroxysuccinimide to form the ester, Compound E. This reaction takes place in the presence of a coupling agent such as 1,3-dicyclohexyl carbodiimide (DCC) and triethylamine in a suitable solvent such as dichloromethane or tetrahydrofuran. The reaction takes place at a temperature of about 0° C. to 25° C. for 2 to 20 hours.

Compound E is reacted with neutralized hydroxylamine in aqueous ethanol to afford Compound F. Compound F is cyclized in situ upon heating at 80° to 100° C. to provide Compound G.

Compound G is subsequently reacted with methoxymethyl chloride to give a protected ether of the N-hydroxy group. This reaction takes place in the presence of a tertiary amine such as diisopropylethylamine in a suitable solvent such as dichloromethane at a temperature of about −40° C. to 0° C. for 0.5 to 4 hours.

Compound H undergoes an aldol condensation with isobutyraldehyde or other suitable agent using lithium hexamethyldisilazide (LHMDS) to afford Compound J as a major isomer in good yield. This reaction takes place in a suitable solvent such as tetrahydrofuran at a temperature of about −78° C. to −80° C., preferably −78° C., for 2 to 6 hours.

Compound J is reacted with methanesulfonyl chloride to give Compound K, the mesylate. This reaction typically takes place in the presence of a tertiary amine such as diisopropylethylamine in a suitable solvent such as dichloromethane at a temperature of about −25° C. to 0° C., preferably −20° to −25° C.

To a cooled solution of Compound K in toluene or other suitable solvent is added 3 equivalents of 1,8-diazabicyclo[5.4.0]-undec-7-ene (DBU). The solution is slowly allowed to warm to room temperature and completion is exhibited in less than 2 hours. Isomeric Compounds $L_1$ and $L_2$ were produced in a ratio of approximately 1:25 to 1:3.

Compound $L_2$ was oxidized with dichlorodicyanobenzoquinone to give Compound M in 30% yield. This reaction is generally conducted in dichloromethane:water (2:1) or other suitable solvent at a temperature of about 0° C. to 30° C. for 10 to 24 hours.

Compound M undergoes deprotection of the MOM group with trifluoroacetic acid in dichloromethane or other suitable solvent to afford Compound II which is identical to the natural product.

Side chain analogs of the natural product, Compound II, can be synthesized in the following manner. Scheme 2 shows the synthetic steps for the synthesis of analogs with the left side chain modified and Scheme 3 shows analogs with the right side chain modified.

Compound H is reacted as previously described with an aldehyde of the formula RCHO, where R is as previously defined, in an aldol reaction, to afford Compound N. This reaction is generally carried out at a temperature of about −78° C. to −60° C. for 2 to 10 hours.

The mesolate, Compound P, is prepared and upon in situ elimination (where R=phenyl), Compound Q is produced in high yield.

Compound Q is oxidized with DDQ to afford Compound R. Deprotection of Compound R gave Compound S. Compounds R and S are crystallized (where R=phenyl) and easily purified without any chromatography.

SCHEME 2

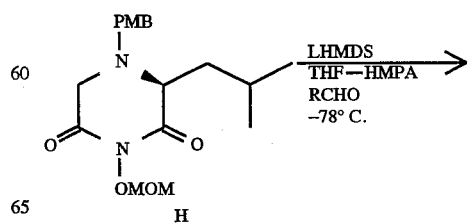

7
-continued
SCHEME 2
8
-continued
SCHEME 3
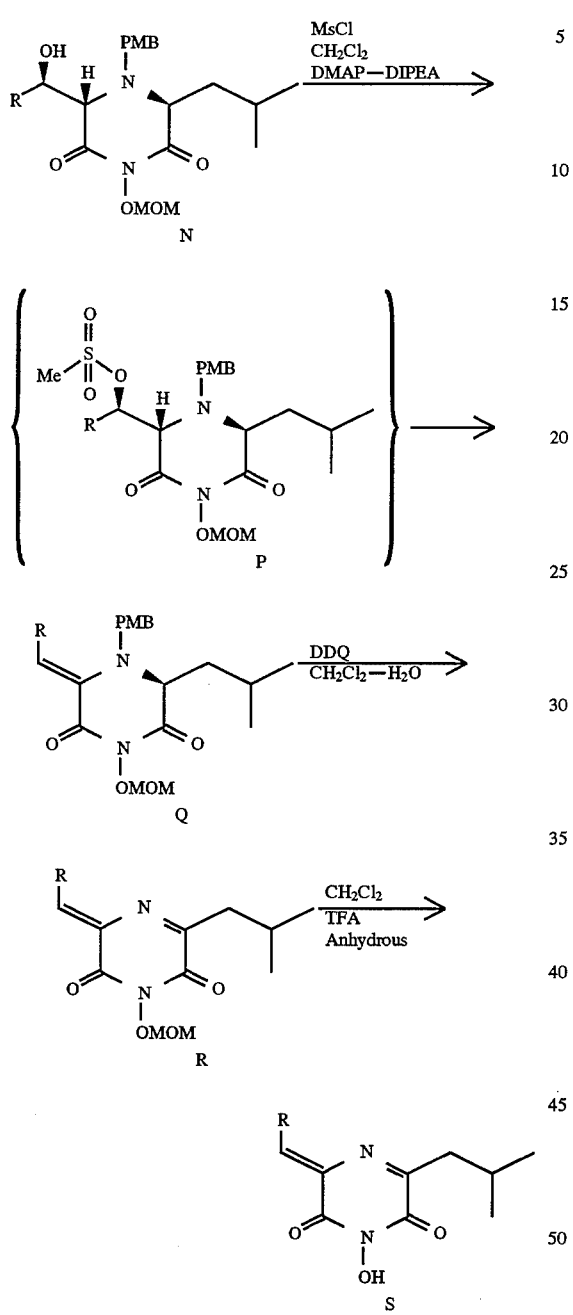
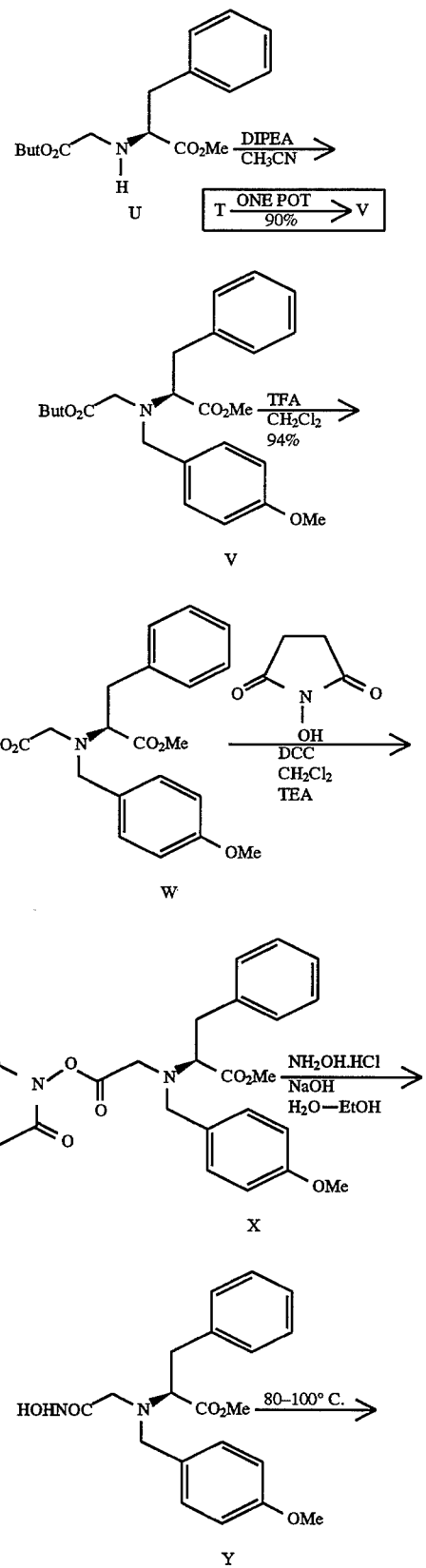
SCHEME 3
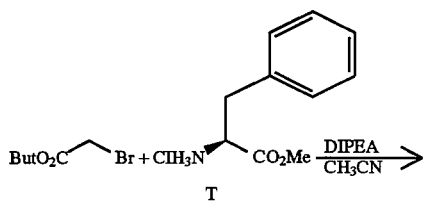

-continued
SCHEME 3

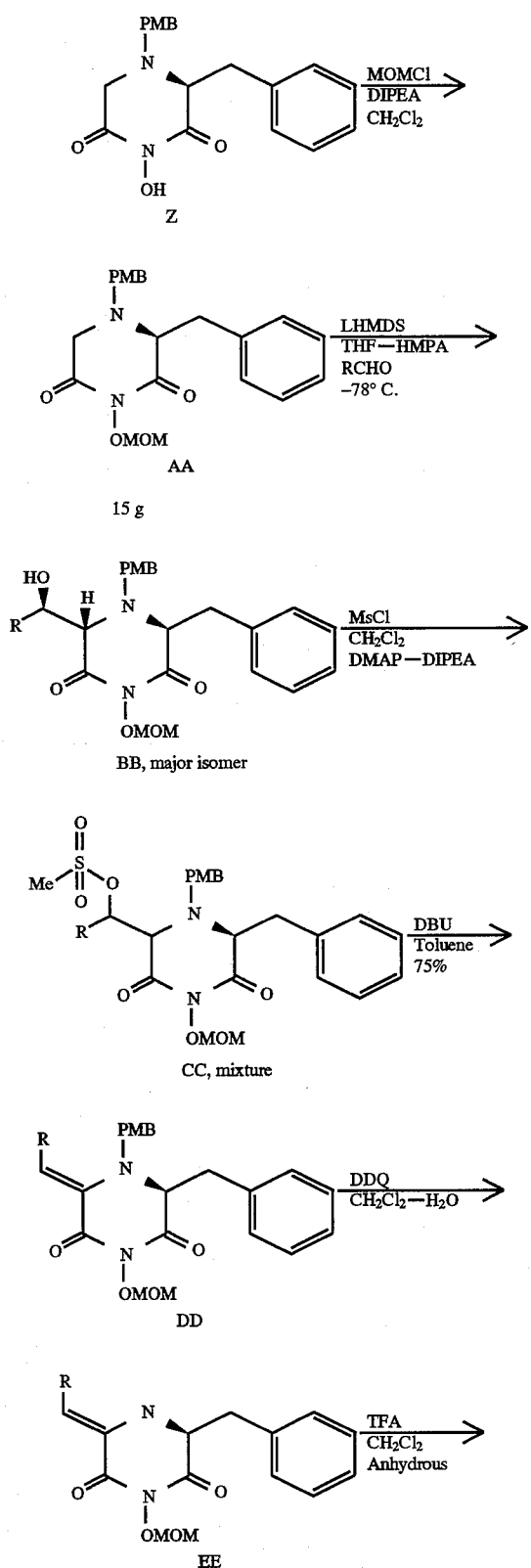
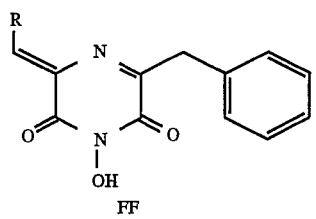

FF

Scheme 3 shows the synthesis of analogs with the right side chain modified. The steps are essentially the same, however, phenyl alanine, Compound T, is employed as a starting material.

The tetrahydro-N-hydroxy analogs can be prepared by careful catalytic hydrogenation of Compound I and analogs thereof using a noble metal catalyst such as palladium or platinum on carbon.

The antiviral properties of the compounds may be determined in an assay which utilizes the unique properties of the virus.

Influenza virus is a negative strand virus with a segmented genome. The synthesis of viral mRNA is accomplished by a virally-encoded transcription complex. Influenza virus is unique in that it requires capped and methylated palmers which are obtained from host cell RNA polymerase H transcripts to initiate mRNA synthesis. An in vitro influenza transcription assay was established to detect agents that may be present in natural product extracts that are capable of inhibiting the transcription apparatus of the influenza virus. The assay is performed in a final volume of 75 μl using 1.5 μg of detergent-disrupted virus, 150 ng of a capped and methylated RNA obtained from alfalfa mosaic virus (ALMV) $RNA_4$, in the presence of 100 mM Tris-HCl pH 7.8, 120 mM KCl, 1 mM dithhiothreitol, 5 mM $MgCl_2$, 0.25% Triton N-100, 0.1 mg/ml tRNA (transfer RNA), 100 μM ATP, 50 μM GTP, 50 μM CTP and 1 μM UTP plus 1 μCi of [$^{35}S$]-UTP.

In carrying out the assay, virus mix of the following composition is first prepared:

|  | μl/assay |
|---|---|
| Sterile $H_2O$ | 2.67 μl |
| 10X Buffer | 7.50 μl |
| 10X NTPs | 7.50 μl |
| RNase free tRNA | 0.75 μl |
| $^{35}$S-UTP | 0.08 μl |
| Virus | 1.50 μl |
| TOTAL VOLUME | 20.0 μl |

To each well of a sterile 96-well microtiter plate, is added 20 microliters of the virus mix thus prepared, 5 microliters of sample and a total of 45 microliters of water. Ten microliters of primer (alfalfa mosaic virus (ALMV) RNA at 0.015 μg/ml) is rapidly thawed at 37° C. and added to all wells except blanks to which ten microliters of water are added instead of the primer.

The plates are gently mixed on the shaker for 30 seconds and then incubated for 60 minutes in a 31° C. water bath.

At the end of this period, the plates are removed from the water bath, placed on a bed of ice and the reaction stopped with (i) 75 μl of sterile saturated sodium pyrophosphate solution containing 0.5 mg/ml RNase-free tRNA and (ii) 50

μl of ice-cold 40% TCA, and the plates allowed to stand on ice for 15 minutes. The samples are then collected, using a cell harvester, washed twice with 5% TCA, then twice with 95% ethanol and then transferred to sealing bags, 20 milliliters of cocktail added and the samples counted for 2 minutes using $^{35}S$ channel in the LKB beta-counter. From the counts obtained, the effect of the claimed compound was compared to a solvent control and the percent inhibition (% I) was calculated as follows:

$$\% I = \frac{DPM \text{ (solvent control)} - DPM \text{ (sample)}}{DPM \text{ (solvent control)} - DPM \text{ (unprimed control)}}$$

Results of this assay for representative compounds prepared by the method of this invention are presented below.

| Compound | $IC_{50}$ μm Influenza Transcription |
| --- | --- |
| I | 5 μM |
| Example 8 | 4.8 |
| Example 9 | 0.9 |
| Example 10 | 7.3 |
| Example 11 | 1.5 |
| Example 12 | 0.8 |
| Example 14 | 2.8 |
| Example 15A | 3.5 |
| Example 15B | 6.5 |
| Example 16 | 85 μM |

The outstanding properties of the compounds of the invention are most effectively utilized when formulated into novel pharmaceutical compositions with a pharmaceutically acceptable carrier according to conventional pharmaceutical compounding techniques.

The novel composition may contain at least a therapeutic amount of the active compound. Generally, the composition contains at least 1 percent by weight of the active compound. Concentrate compositions suitable for dilution prior to use may contain 90 percent or more by weight. The compositions may be suitable for oral, topical, parenteral (including subcutaneous, intramuscular, and intravenous), pulmonary (nasal or buccal inhalation), other nasal and suppository administration or insufflation. The composition may be prepacked by combining the compound with the components suitable for the composition desired.

When oral administration is to be employed, it may be with a liquid composition or a solid composition. For liquid preparations, the therapeutic agent is formulated with liquid carriers such as water, glycols, oils, alcohols and the like. For solid preparations such as capsules and tablets, one or more carriers may be employed. Representative examples of solid carriers include starches, sugars, cellulosic compounds, kaolin and talc. Lubricants, such as calcium or magnesium stearate, together with binders, disintegrating agents and the like are also typically employed. Because of their ease in administration, tablets and capsules represent the most advantageous oral dosage form.

When administration is to be by injection, it may be presented in ampules or in multidose containers, if necessary with an added preservative. The compositions may also take such forms as suspensions, solutions or emulsions in oily or aqueous vehicles such as 0.85 percent sodium chloride or 5 percent dextrose in water, and may contain formulating agents such as suspending, stabilizing and/or dispersing agents. Buffering agents as well as additives such as saline or glucose may be added to make the solutions isotonic. The drug also may be solubilized in alcohol/propylene glycol or polyethylene glycol for drip intravenous administration.

Alternatively, the active ingredients may be in powder form for reconstituting with a suitable vehicle prior to administration.

When administration is to be by inhalation, the compound is conveniently delivered in the form of an aerosol spray presentation from pressurized packs of nebulizers. The preferred delivery system for inhalation is a metered dose inhalation (MDI) aerosol, which may be formulated as a suspension or solution of Compound I in suitable propellants, such as fluorocarbons or hydrocarbons.

It is especially advantageous to formulate the compositions in unit dosage form (as hereinafter defined) for ease of administration and uniformity of dosage. The term "unit dosage form" refers to physically discrete units, each unit containing a predetermined quantity of active ingredient which singly or in multiples would produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of Compound I. Compositions in unit dosage form constitute an aspect of the present invention.

Preferred compounds of the invention include:

1-(N-hydroxy)-3-(2-methyl-propyl)-5-(2-methyl-Z-prop-1-enyl)-2,6-diketopiperazine-3,4-ene, 1-(N-hydroxy)-3-(2-methyl-propyl)-5-(Z-benz-1-enyl)-2,6-diketopiperazine-3,4-ene, 1-(N-hydroxy)-3-(2-methyl-propyl)-5-(Z-p-fluoro-benz-1-enyl)-2,6-diketopiperazine-3,4-ene, 1-(N-hydroxy)-3-(2-methyl-propyl)-5-(Z-o-fluoro-benz-1-enyl)-2,6-diketopiperazine-3,4-ene, 1-(N-hydroxy)-3-(2-methyl-propyl)-5-(Z-m-fluoro-benz-1-enyl)-2,6-diketopiperazine-3,4-ene, 1-(N-hydroxy)-3-(2-methyl-propyl)-5-(Z-p-methoxy-benz-1-enyl)-2,6-diketopiperazine-3,4-ene, 1-(N-hydroxy)-3-(benzyl)-5-(Z-p-methoxybenz-1-enyl)-2,6-diketopiperazine-3,4-ene, and 1-(N-hydroxy)-3-(benzyl)-5-(Z-p-fluoro-benz-1-enyl)-2,6-diketopiperazine-3,4-ene.

The following examples illustrate the invention but are not to be construed as limiting.

PREPARATIVE EXAMPLE 1

Synthesis of N-(p-methoxybenzyl), N-(tert-butyl acetyl)-(S)-leucinemethyl ester

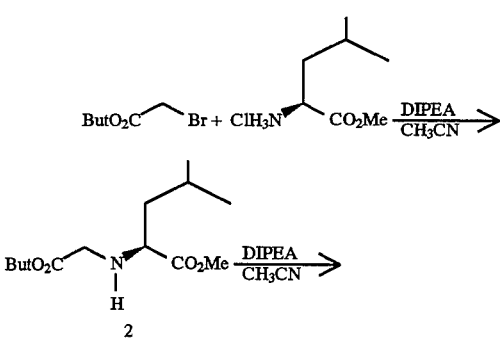

-continued

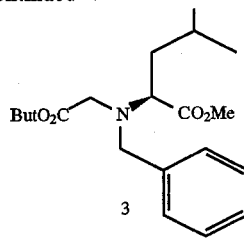

a. A solution of bromo-tert-butyl acetate (44.4 mL, 0.275 mol), (S)-leucine methyl ester hydrochloride (50 g, 0.275 mol) and diisopropylethyl amine (191 mL, 1.1 mol) in acetonitrile (400 mL) was stirred at room temperature for 16 hrs and heated at 60° C. for 4 hrs. After completion of the reaction (TLC, hexane-ethyl acetate, 9:1) a small aliquot (5 mL) was taken out and acetonitrile was removed under reduced pressure. Ethyl acetate (100 mL) was added and the solution was washed with water (2×100 mL), 10% aqueous citric acid (100 mL) and water (100 mL). The ethyl acetate extract was dried over sodium sulfate, evaporated under reduced pressure and chromatographed over silica gel column. Elution with 5% ethyl acetate in hexane gave pure N-tert-butyl acetyl-(S)-leucine methyl ester (2) as an oil, $[\alpha]D^{25}$–17.2 (c, 2.9, MeOH); $^1$H NMR (CDCl$_3$): 0.88 (3H, d, J=6.6 Hz), 0.89 (3H, d, J=6.6 Hz), 1.42 (9H, s), 1.48 (2H, m), 1.70 (1H, apparent hept, J=6.6 Hz), 3.24 (2H, ABq, J=18 Hz), 3.29 (1H, t, J=7.2 Hz), 3.68 (3H, s); $^{13}$C NMR (CDCl$_3$): 22.34 (CH$_3$), 22.65 (CH$_3$), 24.81 (CH), 28.06 (C(CH$_3$)$_3$), 42.44 (CH$_2$), 49.86 (CH$_2$), 51.74 (OCH$_3$), 59.22 (CH), 81.26 (C), 170.87 (CO), 175.43 (CO).

| Analysis: | calculated for C$_{13}$H$_{25}$NO$_4$ |
|---|---|
|  | C, 60.20; H, 9.72; N, 5.40 |
| Found: | C, 60.05; H, 9.44; N, 5.32. | b. p-Methoxybenzyl chloride (56 mL, 0.41 mol) was added to aforementioned reaction mixture which was then heated at 70° C. for 24 hrs. After completion of the reaction, the solution was allowed to cool to room temperature. Acetonitrile and DIPEA were removed under reduced pressure and the residue was suspended in 500 mL water. The product was extracted with ethyl acetate (3×600 mL). Ethyl acetate extract was sequentially washed with water (2×400 mL), 10% aqueous citric acid (400 mL), water (400 mL), dried (Na$_2$SO$_4$). The ethyl acetate was removed under reduced pressure and the product was chromatographed over silica gel and eluted with 5% ethyl acetate-hexane to yield an oil of N-(p-methoxybenzyl)-N-(tert-butyl acetyl)-(S)-leucine methyl ester (3, 101.5 g), $[\alpha]D^{25}$–67.8 (c, 3.43, MeOH); $^1$H NMR (CDCl$_3$): 0.73 (3H, d, J=6.6 Hz), 0.86 (3H, d, J=6.6 Hz), 1.43 (9H, s), 1.48 and 1.57 (2H, m), 1.76 (1H, apparent hept, J=6.6 Hz), 3.34 (2H, ABq, J=17.4 Hz), 3.42 (1H, t, J=6.6 Hz), 3.66 (1H, ABd, J=13.5 Hz), 3.69 (3H, s), 3.78 (3H, s), 3.90 (1H, ABd, J=13.5 Hz), 6.83 (2H, d, J=8.7 Hz), 7.30 (2H, d, J=8.7 Hz); $^{13}$C NMR (CDCl$_3$): 21.85 (CH$_3$), 23.06 (CH$_3$), 24.30 (CH), 28.11 (C(CH$_3$)$_3$), 39.15 (CH$_2$), 51.14 (OCH$_3$), 52.39 (CH$_2$), 55.24 (OCH$_3$), 55.50 (CH$_2$), 60.53 (CH), 80.53 (C), 113.56 (CH), 130.22 (CH), 131.02 (C), 158.76 (C), 171.11 (CO), 173.95 (CO).

| Analysis: | calculated for C$_{21}$H$_{33}$NO$_5$ |
|---|---|
|  | C, 66.46; H, 8.76; N, 3.69 |
| Found: | C, 66.75; H, 8.93; N, 3.64. |

PREPARATIVE EXAMPLE 2

Synthesis of N-(p-methoxybenzyl), N-(tert-butyl acetyl)-(S)-phenylalanine-methyl ester

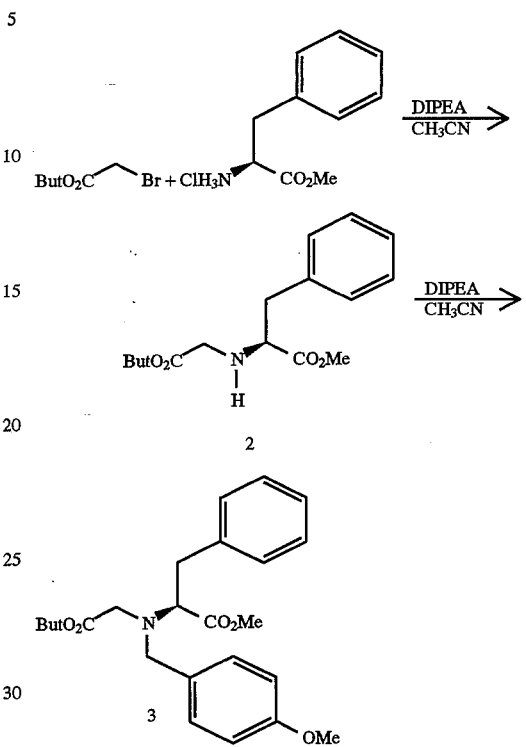

(S)-Phenylalanine methyl ester hydrochloride (20 g, 92.7 mmol) was reacted with bromo-tert-butyl acetate (16.07 mL, 98 mmol) in acetonitrile for 6 hrs before addition of p-methoxy-benzyl chloride (18.85 mL, 139 mmol) and then heated at 70° C. overnight. The reaction was worked up and chromatographed as described above to give pure N-(p-methoxybenzyl)-N-(tert-butyl acetyl)-(S)-leucine methyl ester (3, 34.0 g), $^1$H NMR (CDCl$_3$): 1.44 (9H, s), 2.95 (1H, dd, J=13.5, 7.2 Hz), 3.04 (1H, dd, J=13.8, 8.1 Hz), 3.40 (2H, ABq, J=17.4 Hz), 3.64 (3H, s), 3.64 (1H, dd, J=7.2, 8.1 Hz), 3.74 (1H, d, J=13.5 Hz), 3.78 (3H, s), 3.94 (1H, d, J=13.5 Hz), 6.76 (2H, d, J=9.0 Hz), 7.10 (2H, d, J=8.7 Hz), 7.11 (2H, dd, J=8.1, 1.5 Hz), 7.22 (3H, m); $^{13}$C NMR (CDCl$_3$): 28.13 (3C0, 36.44, 51.28, 52.18, 55.24, 55.44, 64.31, 80.76, 113.52 (2C), 126.32, 128.22 (2C), 129.36 (2C), 130.01 (2C), 130.60, 137.98, 158.68, 170.82, 172.72.

PREPARATIVE EXAMPLE 3

Synthesis of N-(p-methoxybenzyl), N-(carboxymethyl)-(S)-leucinemethyl ester

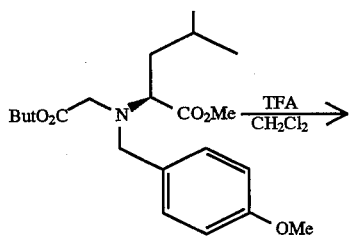

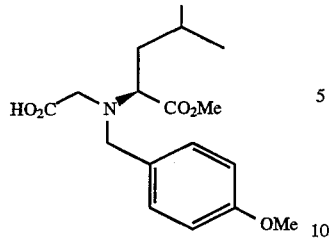

To a solution of tert-butylester (114 g, 0.3 mol) in methylene chloride (200 mL) at −78° C. was added trifluoroacetic acid (160 mL). After stirring the solution for 20 minutes at −78° C., it was allowed to warm to room temperature and stirred for 70 hrs. Volatile material was removed under reduced pressure. Ethyl acetate (2.0 L) was added to the residue followed by 100 mL water. The pH of the solution was 1.0 which was basified to pH 4.0 by addition of 10% aqueous sodium bicarbonate. The layers were separated and the ethyl acetate solution was washed once with 400 mL of water. The product was extracted from ethyl acetate solution by extraction with 10% aqueous sodium bicarbonate (3×300 mL), 4N sodium hydroxide (400 mL) and water (200 mL). The ethyl acetate extract was dried over sodium sulfate and concentrated to give unreacted staffing material (30 g). All of the basic extracts containing the product were combined and acidified to pH 4.0 by addition of aqueous citric acid and extracted with ethyl acetate (3×500 mL). Combined ethyl acetate extract was washed with water (400 mL), dried over sodium sulfate and evaporated under reduced pressure followed by drying at 60° C. under vacuum for 48 hrs gave pure acid 67 g, 93.7% based on recovery of starting material) as a gum. A small portion was purified on a preparative Zorbax RX C-8 (22.5×250 mm) HPLC column and eluted with 30% aqueous acetonitrile at a flow rate of 10 mL per minute to give the analytical sample. $[\alpha]D^{25}$−33.8 (c, 0.32, $CH_3OH$); $^1H$ NMR ($CDCl_3$): 0.85 (3H, d, J=6.3 Hz), 0.90 (3H, d, J=6.0 Hz), 1.68 (2H, m), 1.83 (1H, m), 3.81 (3H, s), 3.82 (3H, s), 3.96 (2H, ABq, J=17.4), 4.05 (1H, dd, J=8.7, 4.8 Hz), 4.27 (2H, s), 6.92 (2H, d, J=8.7 Hz), 7.33 (2H, d, J=8.7 Hz), 9.34 (OH); FABMS (m/z): 330 (M+Li), 324 (M+H).

| Analysis: | calculated for $C_{17}H_{25}NO_5$.0.7 TFA |
| --- | --- |
| | C, 54.81; H, 6.42; N, 3.49 |
| Found: | C, 54.89; H, 6.25; N, 4.03. |

PREPARATIVE EXAMPLE 4

Synthesis of N-(p-methoxybenzyl), N-(carboxymethyl)-(S)-phenylalanine-methyl ester

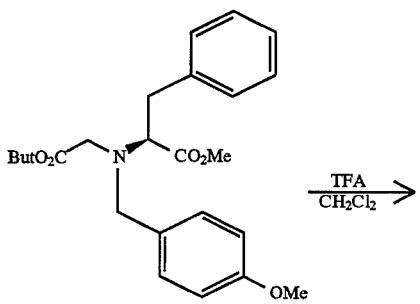

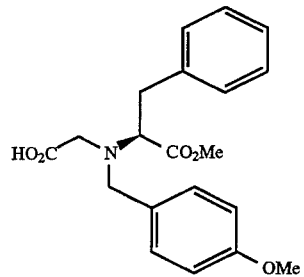

Tert-Butylester (33 g, 80 mmol) in methylene chloride (160 mL) was deprotected with trifluoroacetic acid (40 mL) by stirring at room temperature for 48 hrs. The solvents were removed under reduced pressure and the product was thoroughly dried under vacuum for 48 hrs and the acid was used for next step without any purification. $^1H$ NMR ($CDCl_3$): 3.24 (1H, dd, J=13.5, 8.1 Hz), 3.34 (1H, dd, J=13.5, 7.5 Hz), 3.74 (3H, s), 3.79 (3H, s), 4.14 (2H, s), 4.34 (2H, ABq, J=12.9 Hz), 4.40 (1H, dd, J=8.1, 7.5 Hz), 6.86 (2H, d, J=8.7 Hz), 7.07 (2H, m), 7.18 (2H, d, J=9.0 Hz), 7.31 (3H, m).

PREPARATIVE EXAMPLE 5

Synthesis of 1-(N-hydroxy-methoxymethyl)-3-(2-methylpropyl)-4-(N-para-methoxybenzyl)-2,6-diketopiperazine

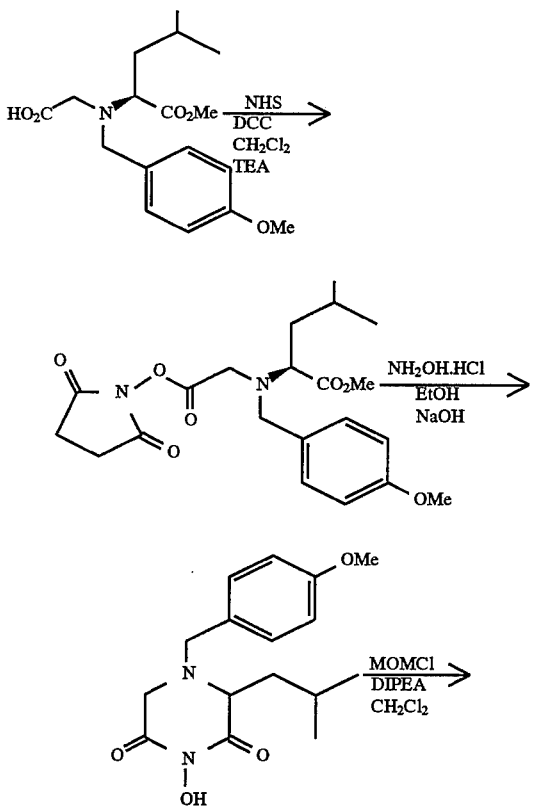

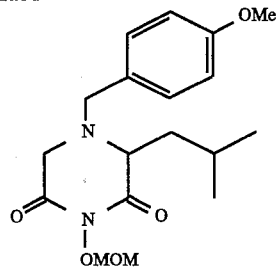

a. N-Hydroxy succinimide (NHS) (23.0 g, 0.2 mol) and triethylamine (27.8 mL, 0.2 mol) was added to a solution of acid (64.6 g, 0.2 mol) in methylene chloride (500 mL). The solution was cooled to 0° C. and DCC (41.2 g, 0.2 mol) was added in a small portions over a period of 5 minutes. The solution was stirred under nitrogen for 20 hrs at room temperature. The precipitated urea was removed by filtration and the filtrate was concentrated to dryness under reduced pressure to give 90 g of chromatographically homogeneous (TLC: hexane-ethyl acetate, 7:3) succinimide ester as a gum which was used in to next step without purification. 1H NMR (CDCl$_3$): 0.70 (3H, d, J=6.6 Hz), 0.86 (3H, d, J=6.6 Hz), 1.54 and 1.61 (2H, m), 1.73 (1H, m), 2.84 (4H, s), 3.46 (1H, dd, J=9.0, 6.3 Hz), 3.69 (1H, d, J=12.9 Hz), 3.71 (3H, s), 3.79 (3H, s), 3.86 (2H, ABq, J=18 Hz), 3.94 (1H, d, J=13.2 Hz), 6.84 (2H, d, J=8.7 Hz), 7.28 (2H, d, J=8.7 Hz); FABMS (m/z): 421 (M+H).

b. To a solution of succinimide ester (84 g, 0.2 mol) in a mixture of ethanol (250 mL) and THF (200 mL) was added a neutralized solution of hydroxylamine [hydroxylamine hydrochloride (20.85 g, 0.3 mol) was dissolved in 100 mL water and was mixed with a 100 mL solution of 0.3 mol sodium hydroxide]. The mixture which had a pH of 6.0 was stirred at room temperature for 3 hrs. TLC examination (hexane-ethyl acetate, 7:3) indicated consumption of the succinimide ester and formation of a ferric chloride positive product. Precipitated sodium chloride was removed from reaction mixture by filtration and the precipitate was washed with 20 mL ethanol. The combined filtrate was refluxed overnight to give almost clean (HPLC: Zorbax RX C-8, 4.6×250 mm, 40% aqueous acetonitrile containing 0.1% TFA, flow rate 1 mL per minute at 40° C., $t_R$ of the product 15.19 minutes) cyclized N-hydroxy compound. After removing most of the solvents from the reaction mixture under reduced pressure, (pH 5.3) the mixture was poured onto 200 mL water thus giving a total volume of 600 mL. The reaction mixture was extracted with ethyl acetate (4×900 mL). Ethyl acetate extract was washed with water (300 mL), dried over sodium sulfate and evaporated under reduced pressure to give ~70 g of crude product as a gum. A small portion was purified on preparative Zorbax RX C-8 (22.5×250 mm) HPLC column and eluted with 30% aqueous acetonitrile containing 0.1% TFA at a flow rate of 10 mL per minutes to give a semi solid; [α]D$^{25}$–21.2 (c, 0.61, CH$_3$OH); $^1$H NMR (CDCl$_3$): 0.80 (3H, d, J=6.3 Hz), 0.94 (3H, d, J=6.3 Hz), 1.28 (2H, m) 1.60 (1H, m), 3.35 (1H, brt), 3.58 (1H, d, J=18 Hz), 3.72 (2H, ABq, J=12.9 Hz), 3.80 (3H, s), 3.87 (1H, d, J=18 Hz), 5.90 (1H, br, OH), 6.86 (2H, d, J=8.7 Hz), 7.17 (2H, d, J=8.4 Hz); $^{13}$C NMR (CDCl$_3$): 21.24, 22.96, 24.67, 37.80, 50.28, 55.32, 58.53, 61.43, 114.09 (2C), 128.12, 130.29 (2C), 159.44, 165.39, 169.03; FABMS (m/z): 367 (M+Na+K–H), 351 (M+2Na–H), 336 (M+Na+Li–H), 319 (M+2Li–H).

| Analysis: | calculated for C$_{16}$H$_{22}$N$_2$O$_4$.0.3 TFA |
| --- | --- |
| | C, 58.54; H, 6.60; N, 8.23 |
| Found: | C, 58.85; H, 6.51; N, 8.50. | c. To a cooled (–40° C.) and stirred (under nitrogen) solution of just prepared N-hydroxy compound (66.8 g, 0.2 mol) in methylene chloride (600 mL) was added diisopropylethyl amine (76 mL, 0.4 mol) followed by addition of methoxymethyl chloride (33.1 mL, 0.4 mol) over 15 minutes. The solution was stirred at the same temperature for 2 hrs. After completion (TLC, hexane-ethyl acetate, 9:1) of the reaction, methylene chloride was removed under reduced pressure and the water (500 mL) was added to residue and product was extracted with ethyl acetate (3×600 mL). The ethyl acetate layer was washed with 10% aqueous citric acid (2×400 mL), water (2×400 mL), dried over sodium sulfate and evaporated under reduced pressure to give ~80 g of an oily product which was chromatographed on a silica gel column. Elution with 5 to 10% of ethyl acetate in hexane gave MOM ether (54 g) as an oil. [α]D$^{25}$–33.8 (c, 0.65, CH$_3$OH); $^1$H NMR (CDCl$_3$): 0.81 (3H, d, J=6.6 Hz), 0.95 (3H, d, J=6.3 Hz), 1.57 and 1.75 (2H, m), 1.87 (1H, m), 3.52 (1H, dd, J=18, 1.2 Hz), 3.61 (1H, dd, J=5.4, 1.2 Hz), 3.63 (3H, s), 3.72 (2H, ABq, J=12.9 Hz), 3.81 (3H, s), 3.82 (1H, d, J=18 Hz), 5.01 (2H, ABq, J=7.0 Hz), 6.86 (2H, d, J=9.0 Hz), 7.17 (2H, d, J=9.0 Hz); $^{13}$C NMR (CDCl$_3$): 21.26, 23.04, 24.48, 37.85, 51.21, 55.31, 58.27, 58.32, 62.36, 100.63, 114.03 (2C), 128.44, 130.31 (2C), 159.36, 167.18, 170.39.

| Analysis: | calculated for C$_{18}$H$_{26}$N$_2$O$_5$ |
| --- | --- |
| | C, 61.70; H, 7.47; N, 7.99 |
| Found: | C, 61.85; H, 7.73; N, 8.16. |

PREPARATIVE EXAMPLE 6

Synthesis of 1-(N-hydroxy-methoxymethyl)-3S-(benzyl)-4-(N-para-methoxybenzyl)-2,6-diketopiperazine.

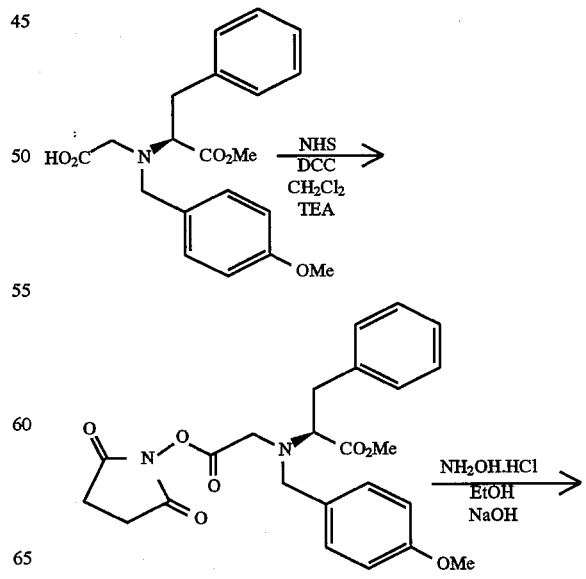

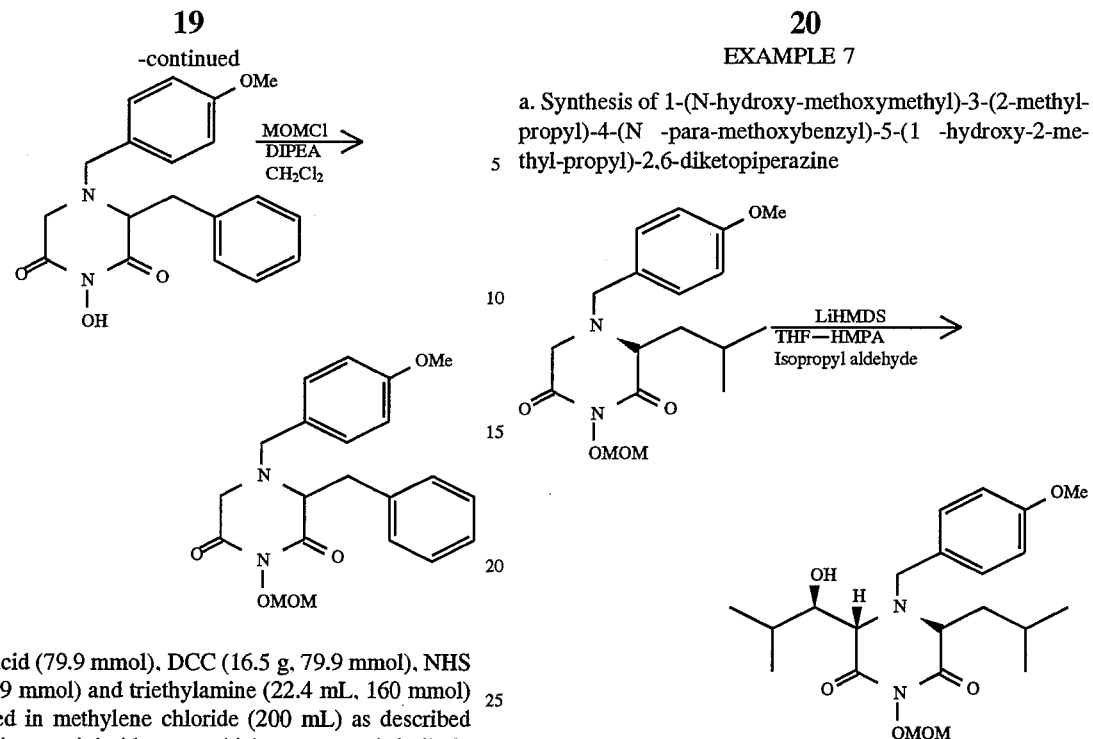

a. The acid (79.9 mmol), DCC (16.5 g, 79.9 mmol), NHS (9.2 g, 79.9 mmol) and triethylamine (22.4 mL, 160 mmol) was reacted in methylene chloride (200 mL) as described above to give succinimide ester which was reacted similarly with hydroxyl amine hydrochloride (8.21 g, 120 mmol) for 48 hrs. The reaction mixture was concentrated under reduced pressure to a volume of 100 mL. The precipitated product (18 g) was collected by filtration and washed with water. The filtrate was extracted with ethyl acetate (3×400 mL) and ethyl acetate layer was washed with water, dried ($Na_2SO_4$) and evaporated under reduced pressure to give 7 g of additional product (total yield 92.0%). Recrystallization from methylene chloride-hexane gave colorless granules, $^1H$ NMR ($CDCl_3$): 3.09 (1H, dd, J=14.1, 9.3 Hz), 3.16 (1H, dd, J=14.1, 5.4 Hz), 3.57 (1H, dd, J=18, 0.9 Hz), 3.68 (2H, ABq, J=13.2 Hz), 3.77 (3H, s), 3.87 (1H, ddd, J=9.3, 5.4, 0.9 Hz), 3.97 (1H, d, J=18 Hz), 6.73 (2H, d, J=8.7 Hz), 6.87 (2H, d, J=8.7 Hz), 7.15 (2H, dd, J=7.8, 2.4 Hz), 7.28 (3H, m), 8.50 (1H, broad signal, OH); $^{13}C$ NMR ($CDCl_3$): 35.19, 50.89, 55.29, 58.22, 64.63, 113.94 (2C), 126.98, 127.96, 128.53 (2C), 129.16 (2C), 129.97 (2C), 136.72, 159.22, 166.25, 168.53.

b. A cooled solution (−40° C.) of the N-hydroxy compound (23 g, 67.6 mmol) in methylene chloride (200 mL) was reacted with methoxy-methyl chloride (10.3 mL, 135 mmol). The reaction was worked up and chromatographed in an analogous manner as described before to give 15 g of the MOM ether as an oil. $^1H$ NMR ($CDCl_3$): 3.09 (1H, dd, J=14.4, 9.3 Hz), 3.16 (1H, dd, J=14.4, 5.7 Hz), 3.54 (1H, dd, J=18.0, 1.2 Hz), 3.64 (3H, s), 3.69 (2H, ABq, J=13.2 Hz), 3.83 (1H, ddd, J=9.0, 5.7, 1.2 Hz), 3.92 (1H, d, J=18.0 Hz), 5.02 (2H, ABq, J=7.2 Hz), 6.75 (2H, d, J=8.7 Hz), 6.90 (2H, d, J=8.7 Hz), 7.16 (2H, dd, J=7.8, 2.1 Hz), 7.23 (3H, m); $^{13}C$ NMR ($CDCl_3$): 35.21, 51.71, 55.28, 57.99, 58.33, 65.41, 100.88, 113.93 (2C), 126.92, 128.05, 128.49 (2C), 129.15 (2C), 130.01 (2C), 136.80, 159.24, 167.10, 169.13.

EXAMPLE 7 a. Synthesis of 1-(N-hydroxy-methoxymethyl)-3-(2-methyl-propyl)-4-(N -para-methoxybenzyl)-5-(1 -hydroxy-2-methyl-propyl)-2,6-diketopiperazine To a cooled (−78° C.) solution of MOM ether (5.5 g, 15.7 mmol) in THF (60 mL) and HMPA (10 mL) was added 1M THF solution of lithium hexamethyl disilazide (18.85 ml, 18.85 mmol) under nitrogen over a period of 10 minutes. The dark yellow solution thus appeared was stirred at the same temperature for 3 hrs. Isopropyl aldehyde (5.7 mL, 62.8 mmol, 4×) was added slowly (10 minutes) via a syringe. The solution which tamed pale was stirred for 2 hrs. The reaction was monitored on a TLC (hexane-ethyl acetate, 3:1 ) and after complete consumption of the starting MOM ether it was quenched with 20 mL of 10% aqueous ammonium chloride. The reaction mixture was allowed to warm to room temperature and poured on to ethyl acetate (800 mL). The organic layer was washed with water (3×300 mL), dried on sodium sulfate, evaporated under reduced pressure to give a gum which was chromatographed over a silica gel column. Elution of the column with 5–20% ethyl acetate in hexane afforded 4.2 g of the aldol product as a gum. $[\alpha]D^{25}$−24.2 (c, 0.54, $CH_3OH$); $^1H$ NMR ($C_6D_6$): 0.52 (3H, d, J=6.5 Hz), 0.74 (3H, d, J=7.0 Hz), 0.88 (3H, d, J=6.5 Hz), 1.03 (3H, d, J=7.0 Hz), 1.41 (2H, t, J=7.5 Hz), 1.73 (1H, nonet, J=6.5 Hz), 2.10 (1H, doublet of heptet, J=7.0, 3.5 Hz), 3.19 (1H, d, J=13 Hz), 3.25 (3H, s), 3.49 (3H, s), 3.58 (1H, d, J=13 Hz), 3.62 (1H, d, J=7.5 Hz), 3.72 (1H, t, J=7.5 Hz), 3.91 (1H, brdd, J=7.0, 2.5 Hz), 4.92 (1H, d, J=7.5 Hz), 5.02 (1H, d, J=7.5 Hz), 6.66 (2H, d, J=8.5 Hz), 6.98 (2H, d, J=9.0 Hz);

| Analysis: | calculated for $C_{22}H_{34}N_2O_6$ |
| --- | --- |
| | C, 62.54; H, 8.11; N, 6.62 |
| Found: | C, 62.65; H, 8.36; N, 6.33. | b. Synthesis of 1-(N-hydroxy-methoxymethyl)-3-(2-methylpropyl)-4-(N-para-methoxybenzyl)-5-(2-methyl-E and Z-prop-1-enyl)-2,6diketopiperazine

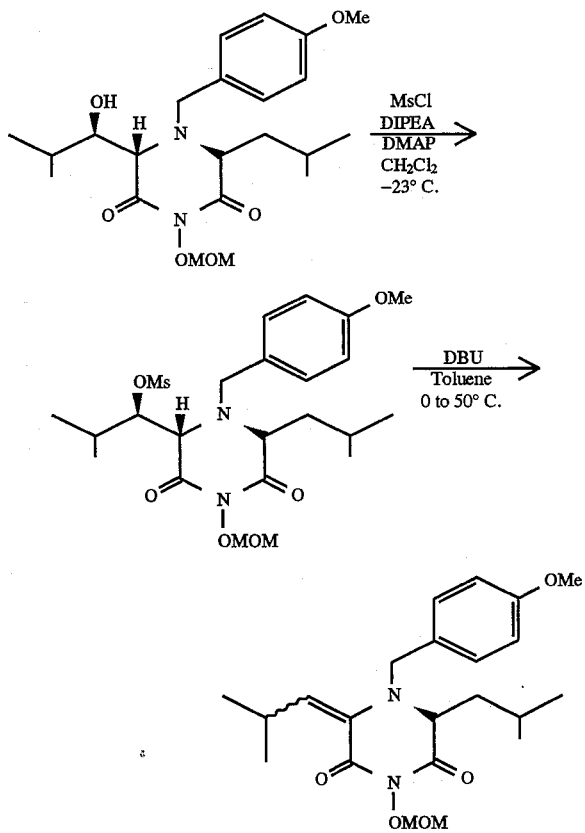

1. Diisopropylethyl amine (3.13 mL, 18 mmol) and dimethylamino pyridine (2.2 g, 18 mmol) was added under nitrogen to a cooled (−23° C.) methylene chloride (50 mL) solution of hydroxy compound (3.8 g, 9 mmol). After 10 minutes methanesulfonyl chloride (1.39 mL, 18 mmol) was slowly added via a syringe and the mixture was stirred for 20 minutes at −23° C. followed by 1 hr at room temperature. TLC examination (hexane-ethyl acetate, 7:3) suggested the formation of a slightly polar (lower RF) product than starting hydroxy compound. The reaction mixture was conveniently monitored on TLC (hexane-ethyl acetate, 7:3). Water (100 mL) was added to the mixture and extracted with ethyl acetate (800 mL). The ethyl acetate layer was washed sequentially with water (2×200 mL), 10% aqueous citric acid (2×200 mL), water (200 mL), 20% aqueous sodium bicarbonate (2×200 mL) and finally with water (2×200 mL), dried over sodium sulfate and evaporated to give chromatographically homogeneous mesolate (4.5 g) as a gum which was used without any purification.

2. To a cooled (0° C.) solution of the mesolate (4.5 g, 9 mmol) in toluene (25 mL) was added DBU (4.0 mL, 27 mmol) via a syringe under nitrogen. The solution was stirred at 0° C. for 10 minutes, room temperature for 30 minutes and at 50° C. for 1 hr. The reaction mixture was allowed to cool to room temperature before adding ethyl acetate (700 mL). The ethyl acetate solution was sequentially washed with water, aqueous citric acid, water, aqueous sodium bicarbonate and water, dried over sodium sulfate, evaporated under reduced pressure to give crude product as a gum which was chromatographed over a silica gel column and eluted with 2 to 15% of ethyl acetate in hexane to give a 400 mg of E-isomer, 800 mg of a mixture of E and Z isomer and finally 1.53 g of Z-isomer all as gums. The isomeric ratio Z/E was measured to be ~3/1 and the overall two step yield was 74.3%.

E-isomer: $[\alpha]D^{25}$+76 (c, 0.25, $CH_3OH$); $^1H$ NMR ($CDCl_3$): 0.81 (3H, d, J=6.4 Hz), 0.83 (3H, d, J=6.4 Hz), 0.93 (3H, d, J=6.4 Hz), 0.98 (3H, d, J=6.4 Hz), 1.41 (1H, ddd, J=14, 7.0, 7.0 Hz), 1.50 (1H, ddd, J=14, 7.0, 7.0 Hz), 1.74 (1H, nonet, J=6.4 Hz), 3.58 (1H, m), 3.63 (3H, s), 3.65 (1H, t, J=8.0 Hz), 3.78 (1H, d, J=12.8 Hz), 3.79 (3H, s), 4.00 (1H, d, J=13.2 Hz), 5.00 (2H, ABq, J=7.2 Hz), 5.44 (1H, d, J=10 Hz), 6.84 (2H, d, J=8.8 Hz), 7.15 (2H, d, J=8.4 Hz); $^{13}C$ NMR ($CDCl_3$): 22.23 ($CH_3$), 22.37 ($CH_3$), 22.69 ($CH_3$), 23.06 ($CH_3$), 24.32 (CH), 26.55 (CH), 38.30 ($CH_2$), 55.27 ($OCH_3$), 56.34 ($CH_2$), 58.17 ($OCH_3$), 60.16 (CH), 100.64 ($OCH_2O$), 113.94 (2×CH), 128.15 (C), 130.18 (2×CH), 130.44 (C), 143.57 (CH), 159.22 (C), 160.27 (C), 169.32 (C); FABMS (m/z): 427 (M+Na), 405 (M+H).

Z-isomer: $[\alpha]D^{25}$+37.6 (c, 0.21, $CH_3OH$); 0.63 (3H, d, J=6.4 Hz), 0.84 (3H, d, J=6.8 Hz), 0.99 (3H, d, J=6.8 Hz), 1.03 (3H, d, J=6.8 Hz), 1.29 (1H, ddd, J=14, 9.6, 4.4 Hz), 1.49 (1H, ddd, J=13.6, 10.8, 4.4 Hz), 1.77 (1H, m), 3.11 (1H, m), 3.55 (1H, dd, J=11.2, 4.4 Hz), 3.62 (3H, s), 3.78 (1H, d, J=12.8 Hz), 3.79 (3H, s), 3.81 (2H, s), 4.95 (2H, ABq, J=7.2 Hz), 6.71 (1H, d, J=11.2 Hz), 6.86 (2H, d, J=8.4 Hz), 7.20 (2H, d, J=8.8 Hz); $^{13}C$ NMR ($CDCl_3$): 20.80 ($CH_3$), 21.34 ($CH_3$), 22.06 ($CH_3$), 23.14 ($CH_3$), 24.11 (CH), 26.84 (CH), 41.10 ($CH_2$), 55.28 ($OCH_3$), 58.14 ($CH_2$), 60.03 ($OCH_3$), 60.80 (CH), 100.68 ($OCH_2O$), 114.00 (2×CH), 128.29 (C), 130.56 (2×CH), 132.67 (C), 147.58 (CH), 159.40 (C), 160.78 (C), 170.78 (C); FABMS (m/z): 427 (M+Na), 405 (M+H).

| Analysis: | calculated for $C_{22}H_{32}N_2O_5$ |
| --- | --- |
| | C, 65.31; H, 7.97; N, 6.92 |
| Found: | C, 65.61; H, 7.65; N, 6.63. | c. Synthesis of 1-(N-hydroxy-methoxymethyl)-3-(2-methylpropyl)-5-(2-methyl-Z-prop-1-enyl)-2,6-diketopiperazine-3,4-ene

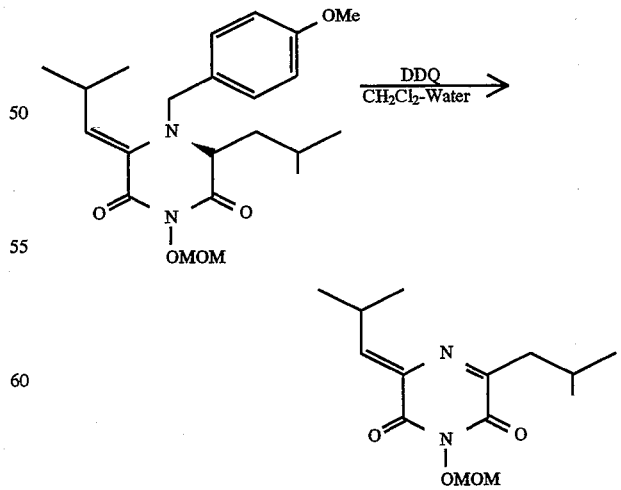

To a solution of N-para-methoxybenzyl compound (96 mg, 0.24 mmol) in methylene chloride (5 mL) was added water (2.5 mL) and DDQ (197 mg, 0.84 mmol, 3.5X) and the reaction mixture was stirred at room temperature overnight. Reaction mixture was filtered through a small bed of silica gel and celite and eluted with 50% ethyl acetate-hexane. The product mixture was rechromatographed over a small silica gel column and eluted with 5% ethyl acetate-hexane to give 20 mg of the chromatographically homogeneous imine product as an oil. $^1$H NMR (CDCl$_3$): 0.99 (3H, d, J=6.8 Hz), 1.13 (3H, d, J=6.4 Hz), 2.19 (1H, heptet, J=6.4 Hz), 2.64 (1H, d, J=6.8 Hz), 3.54 (1H, m), 3.66 (3H, s), 5.08 (2H, s), 7.13 (1H, d, J=10.4 Hz); $^{13}$C NMR (CDCl$_3$): 21.85 (2×CH$_3$), 22.56 (2×CH$_3$), 26.41 (CH), 27.41 (CH), 41.81 (CH$_2$), 58.44 (OCH$_3$), 100.66 (OCH$_2$O), 133.89 (C), 155.29 (C), 157.47 (C), 158.39 (CH), 159.83 (C); FABMS (m/z): 283 (M+H).

| Analysis: | calculated for C$_{14}$H$_{22}$N$_2$O$_4$ |
|---|---|
|  | C, 59.56; H, 7.85; N, 9.92 |
| Found: | C, 59.62; H, 7.42; N, 9.60. | d. Synthesis of 1-(N-hydroxy)-3-(2-methyl-propyl)-5-(2-methyl-Z-prop-1-enyl)-2,6-diketopiperazine-3,4-ene

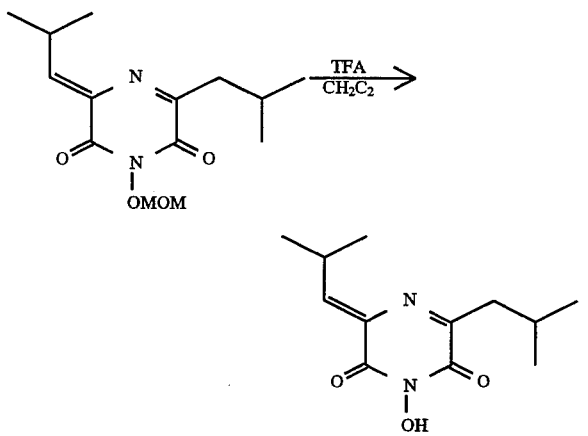

To a cooled (0° C.) solution of MOM ether (6 mg, 0.025 mmol) in anhydrous methylene chloride (1 mL) was added trifluoroacetic acid (TFA) (0.3 mL,) and the solution was stirred under nitrogen for 30 minutes followed by at room temperature for 5 hrs. The progress of the reaction was monitored by TLC (hexane-ethyl acetate, 7:3) and reversed phase HPLC (Zorbax RX C-8, 4.6×250 mm, 50% aqueous acetonitrile +0.1%TFA at 40° C. at a flow rate of 1 ml per minute). After completion of the reaction the volatile materials were evaporated under stream of nitrogen which gave almost pure (NMR and HPLC) product. This was purified on the same analytical HPLC column to give pure product (2 mg) as a gum which was identical with the natural products in all respect (UV, NMR and HPLC) and gave the same IC$_{50}$ in flu transcription assay. $^1$H NMR (CD$_2$Cl$_2$): 0.98 (6H, d, J=6.8 Hz), 1.14 (6H, d, J=6.4 Hz), 2.21 (1H, heptet, J=6.4 Hz), 2.65 (1H, d, J=6.8 Hz), 3.58 (1H, m), 7.21 (1H, d, J=10.4 Hz); FABMS (m/z): 239 (M+H), 283 (M+2Na—H), 393 (M+DTT+H).

In a similar reaction 190 mg of the MOM ether was deprotected and purified on a Zorbax RX C-8 (22×250 mm) column and eluted with 50% aqueous acetonitrile containing 0.1% TFA at a flow rate of 8 mL per minute to give the N-hydroxy product (20 mg).

EXAMPLE 8 a. Synthesis of 1-(N-hydroxy-methoxymethyl)-3-(2-methyl-propyl)-4-para-methoxybenzyl)-5-(1-hydroxy-benzyl-2,6-diketopiperazine

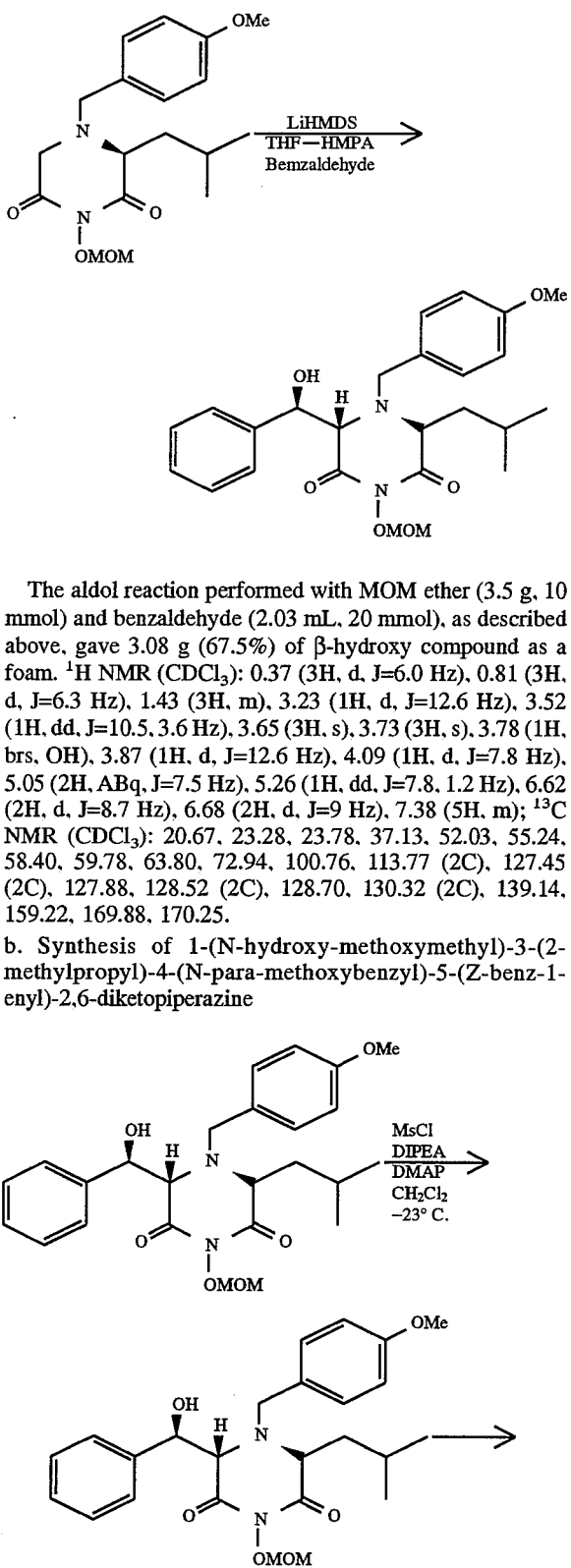

The aldol reaction performed with MOM ether (3.5 g, 10 mmol) and benzaldehyde (2.03 mL, 20 mmol), as described above, gave 3.08 g (67.5%) of β-hydroxy compound as a foam. $^1$H NMR (CDCl$_3$): 0.37 (3H, d, J=6.0 Hz), 0.81 (3H, d, J=6.3 Hz), 1.43 (3H, m), 3.23 (1H, d, J=12.6 Hz), 3.52 (1H, dd, J=10.5, 3.6 Hz), 3.65 (3H, s), 3.73 (3H, s), 3.78 (1H, brs, OH), 3.87 (1H, d, J=12.6 Hz), 4.09 (1H, d, J=7.8 Hz), 5.05 (2H, ABq, J=7.5 Hz), 5.26 (1H, dd, J=7.8, 1.2 Hz), 6.62 (2H, d, J=8.7 Hz), 6.68 (2H, d, J=9 Hz), 7.38 (5H, m); $^{13}$C NMR (CDCl$_3$): 20.67, 23.28, 23.78, 37.13, 52.03, 55.24, 58.40, 59.78, 63.80, 72.94, 100.76, 113.77 (2C), 127.45 (2C), 127.88, 128.52 (2C), 128.70, 130.32 (2C), 139.14, 159.22, 169.88, 170.25.

b. Synthesis of 1-(N-hydroxy-methoxymethyl)-3-(2-methylpropyl)-4-(N-para-methoxybenzyl)-5-(Z-benz-1-enyl)-2,6-diketopiperazine

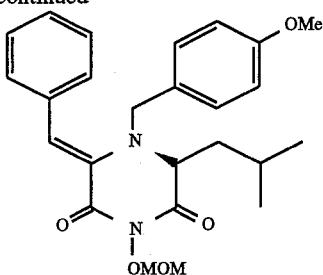

β-Hydroxy benzyl compound (1.42 g, 3.1 mmol) was reacted with methanesulfonyl chloride (2 eq) in an identical condition as described above to give the Z-olefin (1.0 g) as a gum. $^1$H NMR (CDCl$_3$): 0.83 (3H, d, J=6.6 Hz), 0.87 (3H, d, J=6.6 Hz), 1.47 (1H, ddd, J=14.1, 8.7, 5.1 Hz), 1.64 (1H, ddd, J=13.8, 9.9, 5.4 Hz), 1.84 (1H, m), 3.60 (3H, s), 3.72 (1H, dd, J=9.9, 5.1 Hz), 3.78 (3H, s), 3.95 (2H, ABq, J=13.8 Hz), 4.80 (2H, ABq, J=7.2 Hz), 6.83 (1H, d, J=8.7 Hz), 7.12 (1H, d, J=8.7 Hz), 7.44 (2H, m), 7.56 (1H, s), 7.96 (1H, dd, J=8.7, 1.8 Hz); $^{13}$C NMR (CDCl$_3$): 21.41 (CH$_3$), 22.96 (CH$_3$), 24.80 (CH), 42.65 (CH$_2$), 55.27 (OCH$_3$), 58.07 (CH), 59.00 (CH$_2$), 60.07 (OCH$_3$), 100.85 (OCH$_2$O), 114.18 (2×CH), 127.74 (C°), 128.78 (2×CH), 129.86 (CH), 130.54 (2×CH), 130.94 (2×CH), 131.10 (CH), 133.31 (C°), 133.80 (C°), 159.57 (C°), 161.29 (C°), 170.00 (C°).

c. Synthesis of 1-(N-hydroxy-methoxymethyl)-3-(2-methyl-propyl)-5-(Z-benz-1-enyl)-2,6-diketopiperazin-3,4-ene

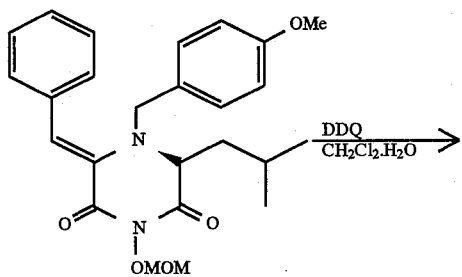

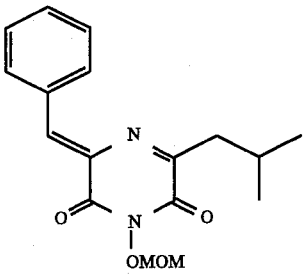

To a solution of the PMB derivative (800 mg, 1.83 mmol) in methylene chloride (10 mL) and water (2 mL) was added DDQ (1.66 g, 4 eq) and stirred overnight. The reaction mixture was filtered and then diluted with 300 mL of methylene chloride and washed with water, 10% aqueous sodium bicarbonate, water, dried (Na$_2$SO$_4$), evaporated under reduced pressure and chromatographed over a silica gel column. Elution with 10% ethyl acetate in hexane yielded 128 mg of the product as a powder. $^1$H NMR (CDCl$_3$): 1.04 (6H, d, J=6.6 Hz), 2.28 (1H, nonet, J=6.6 Hz), 2.75 (2H, d, J=6.9 Hz), 3.69 (3H, s), 5.13 (2H, s), 7.47 (3H, m), 7.83 (1H, s), 8.20 (2H, m); $^{13}$C NMR (CDCl$_3$): 22.62 (2C), 26.49, 42.13, 58.47, 100.72, 128.84 (2C), 131.95, 133.00, 133.67, 134.05 (2C), 142.82, 154.98, 158.28, 160.54.

d. Synthesis of 1-(N-hydroxy)-3-(2-methyl-propyl)-5-(Z-benz-1-enyl)-2,6-diketopiperazine-3,4-ene

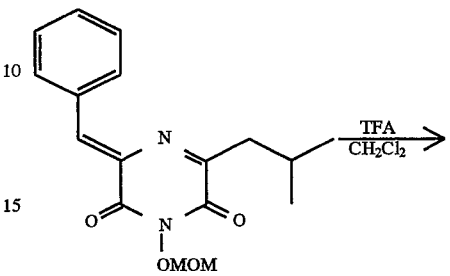

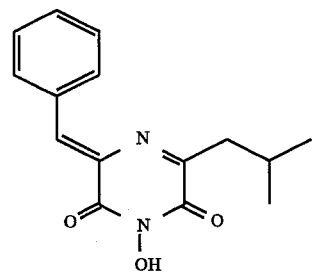

To a cooled (0° C.) solution of MOM ether (35 mg) in methylene chloride (2.0 mL) was added TFA (0.5 mL) and the solution was stirred 30 minutes under nitrogen followed by 5 hrs at room temperature. The solvents were removed under a stream of nitrogen and then dried under vacuum overnight. The residue was crystallized from methylene chloride-hexane to give 25 mg of the N-hydroxy compound as a powder, $^1$H NMR (CDCl$_3$): 1.05 (6H, d, J=6.6 Hz), 2.31 (1H, nonet J=6.6 Hz), 2.79 (2H, d, J=7.2 Hz), 7.48 (3H, m), 7.90 (1H, s), 8.23 (2H, dd, J=8.1, 1.8 Hz); $^{13}$C NMR (CDCl$_3$): 22.58 (2×CH$_3$), 26.51(CH), 42.05 (CH$_2$), 128.98 (2×CH), 131.59 (C°), 132.54 (CH), 133.46 (C°), 134.47 (2×CH), 144.15 (CH), 152.14 (C°), 157.44 (C°), 159.20 (C°).

EXAMPLE 9 a. Synthesis of 1-(N-hydroxy-methoxymethyl)-3-(2-methyl-propyl)-4-(N-para-methoxybenzyl)-5-(1-hydroxy-p-fluoro-benzyl)-2,6-diketopiperazine

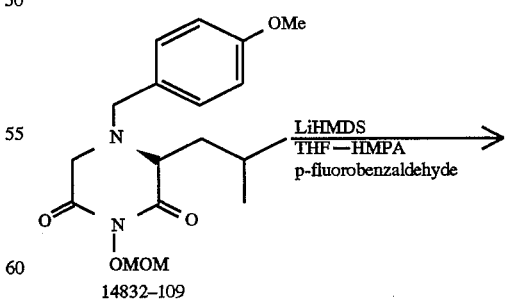

14832-109

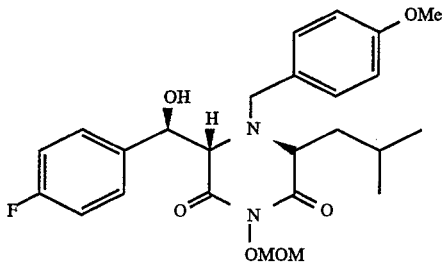

The aldol reaction was repeated with MOM ether (3.5 g, 10 mmol) and p-fluoro-benzaldehyde (2.15 mL, 20 mmol), as described above, to give 3.17 g (67.5%) of β-hydroxy compound as a foam. $^1$H NMR (CDCl$_3$): 0.41 (3H, d, J=6.0 Hz), 0.82 (3H, d, J=6.6 Hz), 1.43 (2H, m), 1.71 (1H, m), 3.23 (1H, d, J=12.9 Hz), 3.54 (1H, dd, J=10.5, 3.9 Hz), 3.64 (3H, s), 3.74 (3H, s), 3.83 (1H, d, J=12.6 Hz), 3.84 (1H, d, J=2.7 Hz, OH), 4.02 (1H, d, J=7.8 Hz), 5.04 (2H, ABq, J=7.5 Hz), 5.23 (1H, dd, J=7.8, 2.7 Hz), 6.66 (2H, d, J=9.0 Hz), 6.70 (2H, d, J=9.0 Hz), 7.07 (2H, t, J=8.7 Hz), 7.31 (2H, dd, J=8.7, 5.4 Hz); $^{13}$C NMR (CDCl$_3$): 20.73, 23.23, 23.85, 37.09, 52.00, 55.26, 58.41, 59.72, 63.90, 72.18, 100.77, 113.87 (2C), 115.38 (d, J=25.7 Hz, 2C), 127.65, 129.12 (d, J=9.8 Hz, 2C), 130.24 (2C), 135.19 (d, J=3.8 Hz), 159.30, 162.78 (d, J=294.8 Hz), 169.79, 170.05.

b. Synthesis of 1-(N-hydroxy-methoxymethyl)-3-(2-methyl-propyl)-4-(N-para-methoxybenzyl)-5-(Z-p-fluoro-benz-1-enyl)-2,6-diketopiperazine

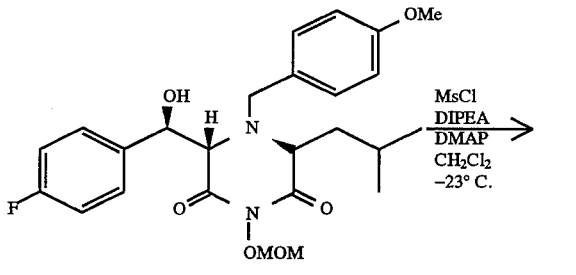

Elimination reaction similar to the one described above from β-Hydroxy benzyl compound (1.42 g, 3.1 mmol) gave the Z-olefin (1.05 g) as a gum. $^1$H NMR (CDCl$_3$): 0.82 (3H, d, J=6.6 Hz), 0.85 (3H, d, J=6.6 Hz), 1.45 (1H, ddd, J=14.1, 8.7, 5.4 Hz), 1.61 (1H, ddd, J=13.8, 9.6, 5.4 Hz), 1.77 (1H, m), 3.58 (3H, s), 3.71 (1H, dd, J=9.6, 5.4 Hz), 3.77 (3H, s), 3.92 (2H, ABq, J=13.8 Hz), 4.80 (2H, ABq, J=7.2 Hz), 6.82 (2H, d, J=8.7 Hz), 7.11 (2H, d, J=8.7 Hz), 7.14 (2H, t, J=8.4 Hz), 7.51 (1H, s), 7.98 (2H, dd, J=8.7, 5.4 Hz); $^{13}$C NMR (CDCl$_3$): 21.40, 22.92, 24.84, 42.49, 55.25, 58.06, 58.93, 60.13, 100.84, 114.20 (2C), 115.93 (d, J=25.8 Hz, 2C), 127.48, 129.99 (d, J=4.3 Hz, 2C), 130.24, 130.56 (2C), 132.96 (d, J=9.8 Hz), 159.62, 161.25, 163.23 (d, J=301.2 Hz), 169.87.

c. Synthesis of 1-(N-hydroxy-methoxymethyl)-3-(2-methyl-propyl)-5-(Z-p-fluoro-benz-1-enyl)-2,6-diketopiperazin-3,4ene.

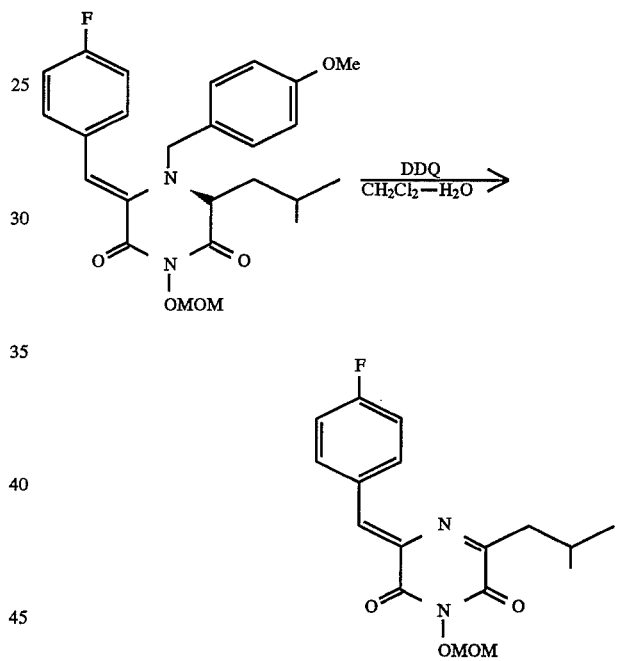

Oxidation of PMB derivative (700 mg, 1.5 mmol) in methylene chloride (10 mL) and water (2 mL) with DDQ (1.60 g, 4 eq) overnight followed by filtration through silica gel and celite and washing of the methylene chloride solution with aqueous sodium bicarbonate and crystallization of the residue from acetone-hexane afforded 180 mg of the desired product as needles. $^1$H NMR (CDCl$_3$): 1.04 (6H, d, J=6.6 Hz), 2.26 (1H, nonet, J=6.9 Hz), 2.75 (2H, d, J=6.9 Hz), 3.69 (3H, s), 5.13 (2H, s), 7.15 (2H, t, J=8.7 Hz), 7.78 (1H, s), 8.23 (dd, J=8.7, 5.7 Hz); $^{13}$C NMR (CDCl$_3$): 22.60 (2C), 26.54, 42.14, 58.48, 100.72, 116.21 (2C, d, J=25.9 Hz), 130.08 (d, J=3.9 Hz), 132.54 (d, J=3.2 Hz), 136.33 (2C, d, J=10.6 Hz), 141.27 (d, J=1.7 Hz), 154.94, 158.4 (d, J=1.7 Hz), 160.49, 164.78 (d, J=306.1 Hz).

d. Synthesis of 1-(N-hydroxy)-3-(2-methyl-propyl)-5-(Z-p-fluorobenz-1-enyl)-2,6-diketopiperazine-3,4-ene

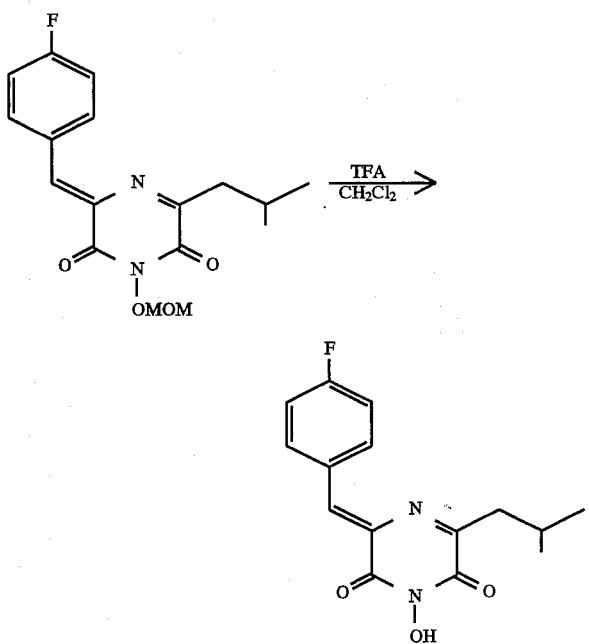

The MOM ether (60 mg) was deprotected with TFA as previously described and crystallized from methylene chloride-hexane to afford the N-hydroxy compound (45 mg) as needles, $^1$H NMR (CDCl$_3$): 1.04 (6H, d, J=6.6 Hz), 2.28 (1H, nonet, J=6.9 Hz), 2.78 (2H, d, J=6.9 Hz), 7.26 (2H, t, J=9.0 Hz), 7.85 (1H, s), 8.27 (2H, dd, J=9.0, 5.7 Hz); $^{13}$C NMR (CDCl$_3$): 22.56 (2C), 26.54, 42.06, 116.39 (2C, d, J=26.1 Hz), 129.90 (d, J=3.9 Hz), 131.19 (d, J=3.2 Hz), 136.82 (2C, d, J=10.9 Hz), 142.53, 152.25, 157.58 (d, J=1.6 Hz), 159.29, 165.12 (d, J=307 Hz).

EXAMPLE 10 a. Synthesis of 1-(N-hydroxy-methoxymethyl)-3-(2-methyl-propyl)-4-(N-para-methoxybenzyl)-5-(1-hydroxy-o-fluoro-benzyl)-2,6-diketopiperazine

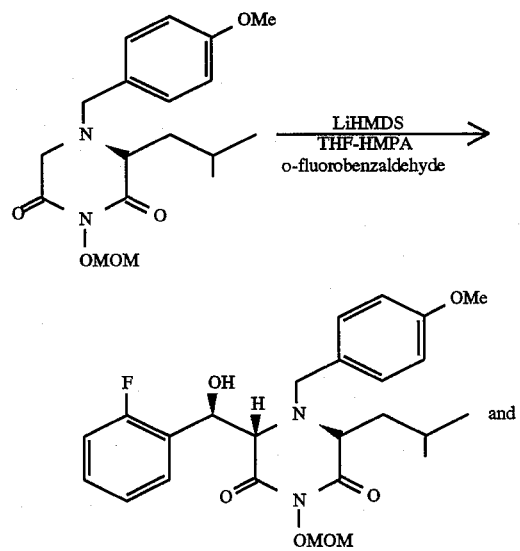

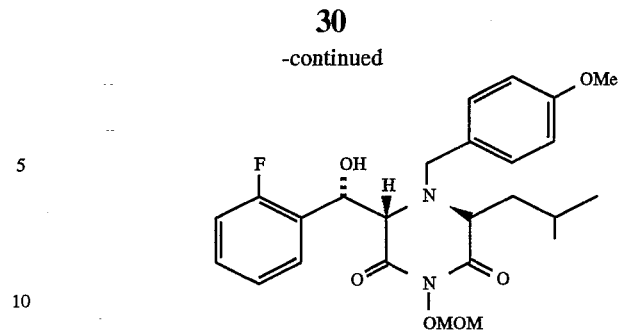

MOM ether (1.75 g, 5 mmol) and O-fluoro-benzaldehyde (1.05 mL, 10 mmol) was reacted as described above to give after chromatography 220 mg of α-hydroxy and 570 mg of β-hydroxy compound, (combined yield 33.3%) both as a gum. $^1$H NMR (CDCl$_3$): 0.78 (3H, brd, J=6 Hz), 0.94 (3H, d, J=6 Hz), 1.28 (2H, m), 1.73 (1H, m), 3.21 (1H, d, J=13.2 Hz), 3.45 (1H, m), 3.64 (3H, s), 3.78 (3H, s), 4.00 (1H, d, J=5.4 Hz), 4.10 (1H, d, J=13.2 Hz), 4.17 (1H, brs, OH), 5.03 (2H, ABq, J=7.2 Hz), 5.63 (1H, dd, J=5.7, 2.7 Hz), 6.70 (2H, d, J=8.4 Hz), 6.76 (2H, d, J=8.4 Hz), 6.95 (1H, dd, J=10.5, 8.1 Hz), 7.20 (1H, dt, J=7.2, 0.6 Hz), 7.30 (1H, m), 7.53 (1H, dt, J=7.5, 1.5 Hz).

β-hydroxy isomer: 1H NMR (CDCl$_3$): 0.34 (3H, d, J=6 Hz), 0.81 (3H, d, J=6 Hz), 1.38 (2H, m), 1.76 (1H, m), 3.24 (1H, d, J=13.9 Hz), 3.54 (1H, dd, J=10.5, 3.6 Hz), 3.65 (3H, s), 3.74 (3H, s), 3.75 (1H, brd, J=3.3 Hz, OH), 3.85 (1H, d, J=12.6 Hz), 4.25 (1H, d, J=8.1 Hz), 5.05 (2H, ABq, J=7.5 Hz), 5.59 (1H, dd, J=8.1, 3.0 Hz), 6.60 (2H, d, J=9.0 Hz), 6.68 (2H, d, J=9.0 Hz), 7.10 (1H, m), 7.19 (1H, dt, J=7.5, 2.1 Hz), 7.40 (2H, m); $^{13}$C NMR (CDCl$_3$): 20.60, 23.15, 23.87, 37.33, 52.29, 55.24, 58.42, 60.09, 62.87, 67.65, 100.78, 113.76 (2C), 115.70 (d, J$_{CF}$=26.5 Hz), 124.40 (d, J$_{CF}$=4.1 Hz), 126.30 (d, J$_{CF}$=15.5 Hz), 127.86, 129.33 (d, J$_{CF}$=4.0 Hz), 130.19 (d, J$_{CF}$=10.3 Hz), 130.28 (2C), 159.22, 160.86 (d, J$_{CF}$=294.3 Hz), 169.91, 170.32.

b. Synthesis of 1-(N-hydroxy-methoxymethyl)-3-(2-methyl-propyl)-4-(N-para-methoxybenzyl)-5-(Z-o-fluoro-benz-1-enyl)-2,6-diketopiperazine

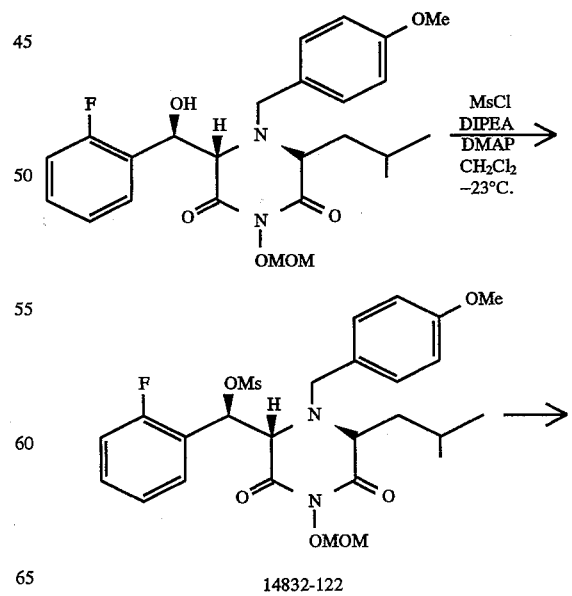

14832-122

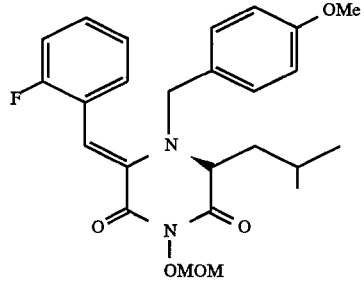

β-Hydroxy-o-fluorobenzyl compound (0.42 g, 0.9 mmol) gave the Z-olefin (0.4 g, 99%) as a gum. $^1$H NMR (CDCl$_3$): 0.84 (3H, d, J=6.6 Hz), 0.89 (3H, d, J=6.6 Hz), 1.49 (1H, ddd, J=13.8, 8.4, 5.4 Hz), 1.65 (1H, ddd, J=13.8, 9.6, 5.7 Hz), 1.81 (1H, m), 3.59 (3H, s), 3.72 (1H, dd, J=9.6, 5.7 Hz), 3.77 (3H, s), 3.87 (1H, d, J=13.8 Hz), 3.99 (1H, d, J=13.8 Hz), 4.83 (2H, ABq, J=7.2 Hz), 6.81 (2H, d, J=8.7 Hz), 7.07 (2H, d, J=8.7 Hz), 7.13 (1H, ddd, J=10.2, 8.4, 1.2 Hz), 7.23 (1H, dt, J=7.2, 0.9 Hz), 7.36 (1H, m), 7.71 (1H, s), 8.27 (1H, dt, J=7.8, 1.8 Hz); $^{13}$C NMR (CDCl$_3$): 21.57, 22.83, 24.84, 42.95, 55.26, 58.10, 59.04, 60.06, 100.83, 114.20 (2C), 115.85 (d, $J_{CF}$=26.4 Hz), 120.42 (d, $J_{CF}$=7.4 Hz), 122.16 (d, $J_{CF}$=13.8 Hz), 124.14 (d, $J_{CF}$=4.4 Hz), 127.69, 130.11 (d, $J_{CF}$=2.3 Hz), 130.34 (2C), 131.16 (d, $J_{CF}$=10.4 Hz), 134.75 (d, $J_{CF}$=1.9 Hz), 159.60, 160.74, 161.18 (d, $J_{CF}$=302.5 Hz), 169.59.

c. Synthesis of 1-(N-hydroxy-methoxymethyl)-3-(2-methyl-propyl)-5-(Z-o-fluoro-benz-1-enyl)-2,6-diketopiperazin-3,4-ene

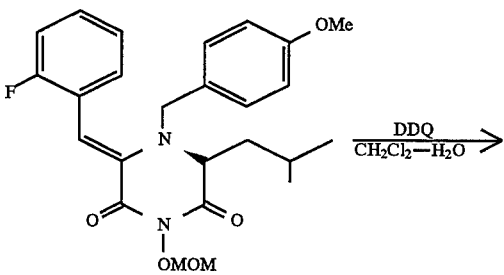

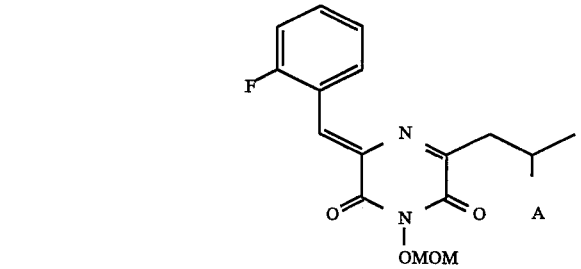

A similar oxidation of PMB derivative (360 mg, 0.82 mmol) with DDQ (0.75 g, 4 eq) overnight followed by crystallization of the residue from methylene chloride-hexane followed by acetone-hexane, furnished 50 mg of desired product A as fine needles. $^1$H NMR (CDCl$_3$): 1.04 (6H, d, J=6.6 Hz), 2.26 (1H, nonet, J=6.9 Hz), 2.75 (2H, d, J=7.2 Hz), 3.69 (3H, s), 5.13 (2H, s), 7.14 (1H, ddd, J=9.5, 8.4, 1.2 Hz), 7.23 (1H, t, J=7.2 Hz), 7.46 (1H, m), 8.16 (1H, s), 7.73 (1H, dt, J=7.8 Hz); $^{13}$C NMR (CDCl$_3$): 22.61 (2C), 26.51, 42.18, 58.49, 100.74, 115.69 (d, $J_{CF}$=26.6 Hz), 121.88 (d, $J_{CF}$=11.6 Hz), 124.45 (d, $J_{CF}$=4.3 Hz), 133.28 (d, $J_{CF}$=9.3 Hz), 133.67 (d, $J_{CF}$=11.1 Hz), 133.82 (d, $J_{CF}$=2.2 Hz), 133.97, 154.88, 159.13, 160.13, 162.69 (d, $J_{CF}$=307.3 Hz).

d. Synthesis of 1-(N-hydroxy)-3-(2-methyl-propyl)-5-(Z-o-fluorobenz-1-enyl)-2,6-diketopiperazine-3,4-ene

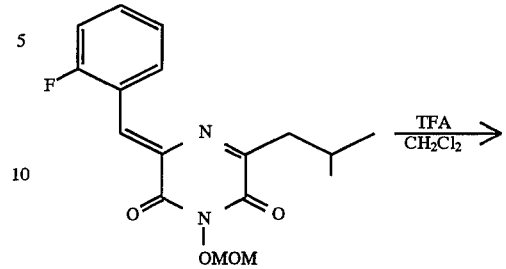

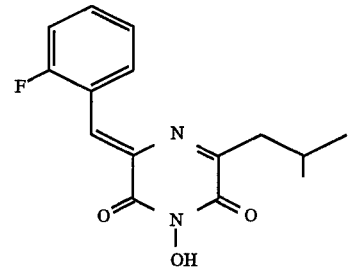

The MOM ether (20 mg) was similarly deprotected with TFA and crystallized from acetone-hexane to give 10 mg of the N-hydroxy compound as needles. $^1$H NMR (CDCl$_3$): 1.04 (6H, d, J=6.6 Hz), 2.30 (1H, nonet, J=6.9 Hz), 2.79 (2H, d, J=7.2 Hz), 7.16 (1H, ddd, J=9.5, 8.4, 1.2 Hz), 7.25 (1H, t, J=5.1 Hz), 7.50 (1H, m), 8.24 (1H, s), 8.78 (1H, dt, J=7.8, 1.8 Hz).

EXAMPLE 11 a. Synthesis of 1-(N-hydroxy-methoxymethyl)-3-(2-methyl-propyl)-4-(N-para-methoxybenzyl)-5-(1-hydroxy-m-fluoro-benzyl)-2,6-diketopiperazine

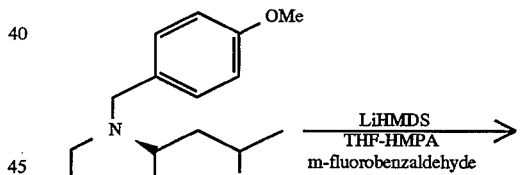

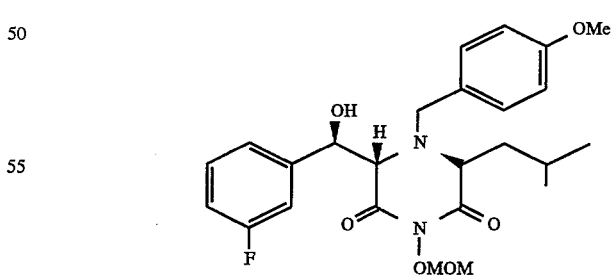

Reaction of MOM ether (1.75 g, 5 mmol) with m-fluorobenzaldehyde (1.06 mL, 10 mmol), as described above, to give 0.95 g (40%) of the β-hydroxy compound as a gum. $^1$H NMR (CDCl$_3$): 0.44 (3H, d, J=6.6 Hz), 0.82 (3H, d, J=6.3 Hz), 1.44 (2H, m), 1.80 (1H, m), 3.23 (1H, d, J=12.9 Hz), 3.58 (1H, dd, J=10.8, 4.2 Hz), 3.63 (3H, s), 3.73 (3H, s), 3.85 (1H, d, J=12.9 Hz), 3.99 (1H, d, J=7.8 Hz), 5.02 (2H, ABq, J=7.5 Hz), 5.22 (1H, d, J=7.5 Hz), 6.70 (4H, brs), 7.07 (3H, m), 7.30 (1H, m).

b. Synthesis of 1-(N-hydroxy-methoxymethyl)-3-(2-methyl-propyl)-4-(N-para-methoxybenzyl)-5-(Z-m-fluoro-benz-1-enyl)-2,6-diketopiperazine

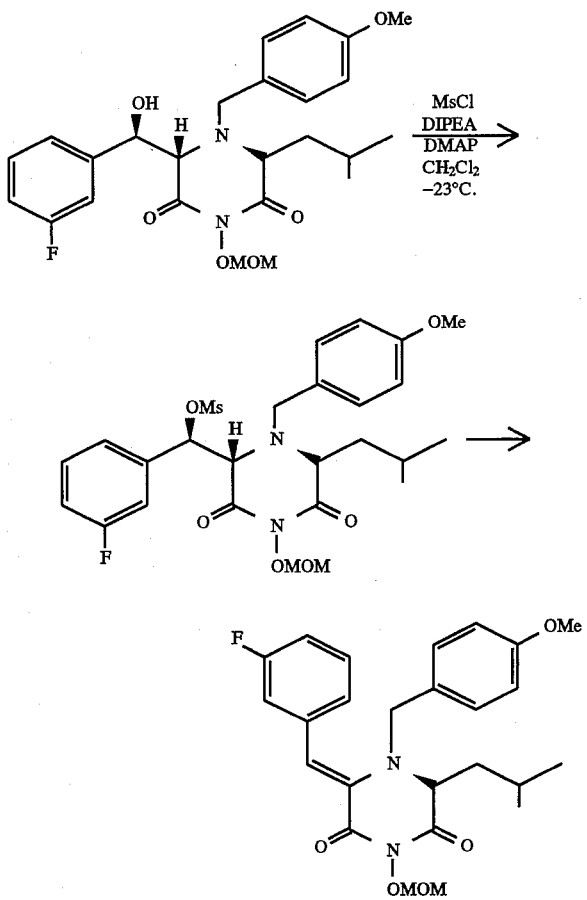

Elimination reaction of β-Hydroxy-m-fluorobenzyl compound (0.75 g, 1.58 mmol) gave the Z-olefin (0.53 g) as a gum, $^1$H NMR (CDCl$_3$): 0.84 (3H, d, J=6.6 Hz), 0.88 (3H, d, J=6.6 Hz), 1.47 (1H, ddd, J=14.1, 8.7, 5.4 Hz), 1.62 (1H, ddd, J=14.1, 9.9, 5.4 Hz), 1.81 (1H, m), 3.60 (3H, s), 3.73 (1H, dd, J=9.9, 5.4 Hz), 3.77 (3H, s), 3.90 (1H, d, J=13.5 Hz), 3.98 (1H, d, J=13.5 Hz), 4.80 (2H, ABq, J=7.2 Hz), 6.83 (2H, d, J=8.7 Hz), 7.10 (1H, m), 7.11 (2H, d, J=8.7 Hz), 7.41 (1H, dt, J=8.1, 6.0 Hz), 7.49 (1H, s), 7.57 (1H, d, J=7.5 Hz), 7.83 (1H, ddd, J=10.5, 2.4, 1.5 Hz); $^{13}$C NMR (CDCl$_3$): 21.40, 22.89, 24.88, 42.76, 55.27, 58.09, 59.23, 60.09, 100.85, 114.24 (2C), 116.70 (d, $J_{CF}$=27.4 Hz), 116.73 (d, $J_{CF}$=27.4 Hz), 127.05 (d, $J_{CF}$=3.3 Hz), 127.41, 129.24 (d, $J_{CF}$=3.4 Hz), 130.20 (d, $J_{CF}$=10 Hz), 130.34 (2C), 134.50, 135.80 (d, $J_{CF}$=9.9 Hz), 159.66, 160.95, 162.80 (d, $J_{CF}$=293.2 Hz), 169.72.

c. Synthesis of 1-(N-hydroxy-methoxymethyl)-3-(2-methyl-propyl)-5-(Z-m-fluoro-benz-1-enyl)-2,6-diketopiperazin-3,4-ene

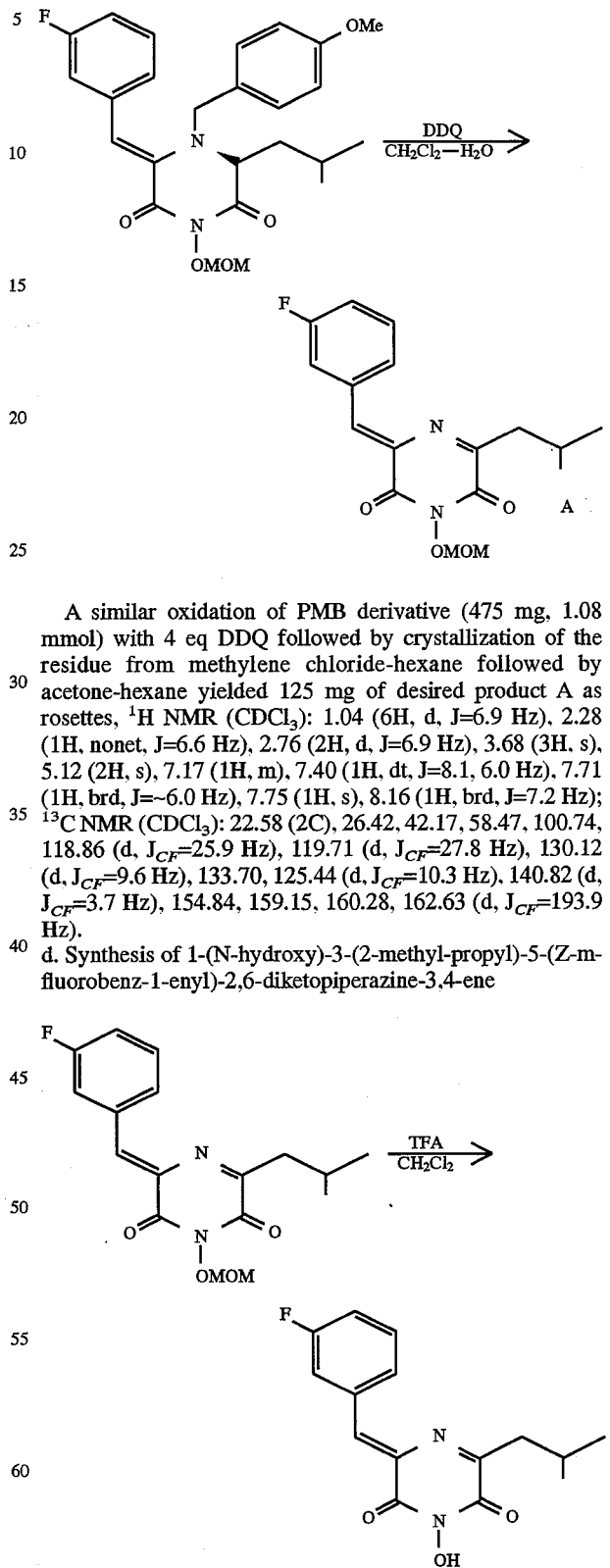

A similar oxidation of PMB derivative (475 mg, 1.08 mmol) with 4 eq DDQ followed by crystallization of the residue from methylene chloride-hexane followed by acetone-hexane yielded 125 mg of desired product A as rosettes, $^1$H NMR (CDCl$_3$): 1.04 (6H, d, J=6.9 Hz), 2.28 (1H, nonet, J=6.6 Hz), 2.76 (2H, d, J=6.9 Hz), 3.68 (3H, s), 5.12 (2H, s), 7.17 (1H, m), 7.40 (1H, dt, J=8.1, 6.0 Hz), 7.71 (1H, brd, J=~6.0 Hz), 7.75 (1H, s), 8.16 (1H, brd, J=7.2 Hz); $^{13}$C NMR (CDCl$_3$): 22.58 (2C), 26.42, 42.17, 58.47, 100.74, 118.86 (d, $J_{CF}$=25.9 Hz), 119.71 (d, $J_{CF}$=27.8 Hz), 130.12 (d, $J_{CF}$=9.6 Hz), 133.70, 125.44 (d, $J_{CF}$=10.3 Hz), 140.82 (d, $J_{CF}$=3.7 Hz), 154.84, 159.15, 160.28, 162.63 (d, $J_{CF}$=193.9 Hz).

d. Synthesis of 1-(N-hydroxy)-3-(2-methyl-propyl)-5-(Z-m-fluorobenz-1-enyl)-2,6-diketopiperazine-3,4-ene

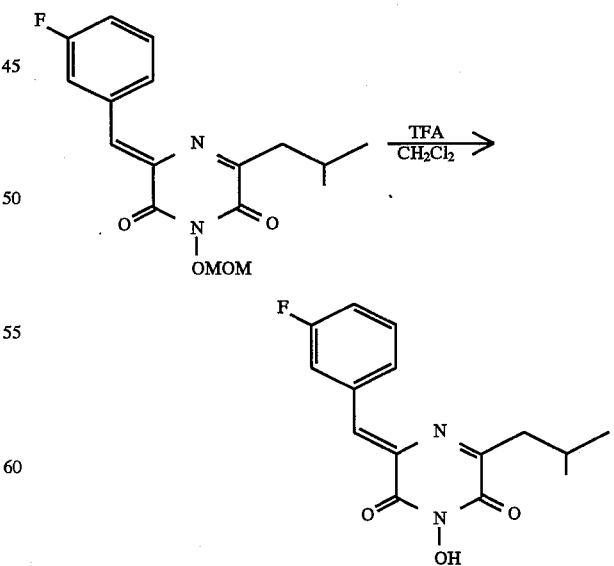

The MOM ether (60 mg) was deprotected with TFA and crystallized from acetone-hexane to give 35 mg of the N-hydroxy compound as needles. $^1$H NMR (CDCl$_3$): 1.05 (6H, d, J=6.9 Hz), 2.30 (1H, nonet, J=6.9 Hz), 2.78 (2H, d, J=7.2 Hz), 7.21 (1H, ddt, J=8.4, 2.7, 1.2 Hz), 7.43 (1H, dt, J=8.1, 6.0 Hz), 7.77 (1H, d, J=7.8 Hz), 7.82 (1H, s), 8.18 (1H, dt, J=10.5, 2.2, 2.0 Hz).

EXAMPLE 12 a. Synthesis of 1-(N-hydroxy-methoxymethyl)-3-(2-methyl-propyl)-4-(N-para-methoxybenzyl)-5-(1-hydroxy-p-methoxybenzyl)-2,6-diketopiperazine

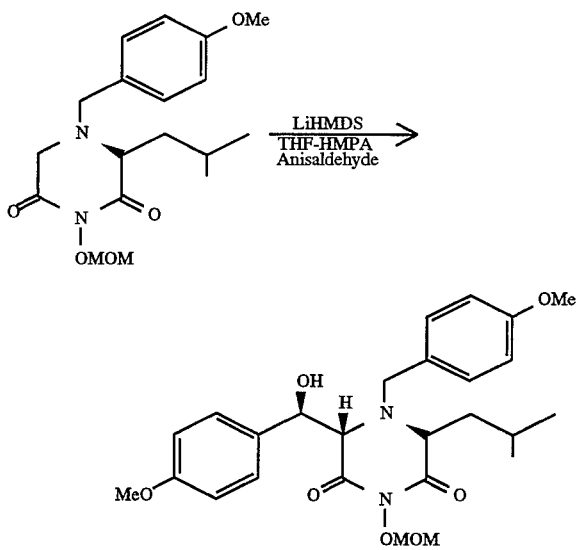

In an identical reaction condition as described above, MOM ether (1.55 g, 4.42 mmol) was reacted with p-methoxybenzaldehyde and LHMDS in THF-HMPA and chromatographed over silica gel column to give β-hydroxy product (1.2 g) as a gum. $^1$H NMR (CDCl$_3$): 0.40 (3H, d, J=6.0 Hz), 0.83 (3H, d, J=6.3 Hz), 1.44 (2H, m), 1.75 (1H, m), 3.23 (1H, d, J=13.8 Hz), 3.53 (1H, dd, J=10.5, 3.9 Hz), 3.66 (3H, s), 3.75 (3H, s), 3.85 (3H, s), 3.87 (1H, d, J=12.9 Hz), 4.08 (1H, d, J=7.8 Hz), 5.05 (2H, ABq, J=7.5 Hz), 5.24 (1H, d, J=7.8 Hz), 6.66 (2H, d, J=9.0 Hz), 6.71 (2H, d, J=9.0 Hz), 6.93 (2H, d, J=9.0 Hz), 7.29 (2H, d, J=8.7 Hz); $^{13}$C NMR (CDCl$_3$): 20.72, 23.28, 23.81, 37.17, 52.00, 55.26, 55.45, 58.40, 59.76, 63.76, 72.51,100.77, 113.79 (2C), 113.90 (2C), 127.92, 128.66 (2C), 130.34 (2C), 131.37, 159.23, 159.84, 170.01,170.23; FABMS (m/z): 487 (M+H), 493 (M+Li).

b. Synthesis of 1-(N-hydroxy-methoxymethyl)-3-(2-methyl-propyl)-4-(N-para-methoxybenzyl)-5-(Z-p-methoxybenz-1-enyl)-2,6-diketopiperazine

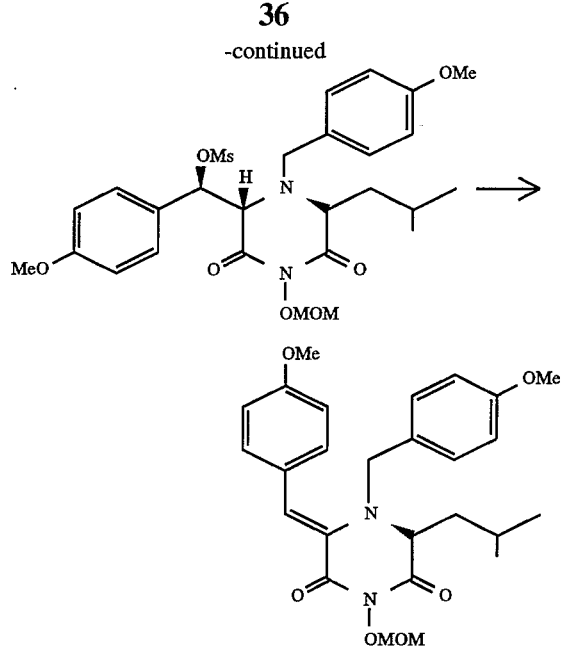

To a cooled (–23° C.) and stirred solution of the hydroxy compound (720 mg, 1.48 mmol) in methylene chloride (10 ml) was added DIPEA (0.52 mL, 2.96 mmol) and DMAP (361 mg, 2.96 mmol) followed by slow addition of methanesulfonyl chloride (0.23 mL, 2.96 mmol) via a syringe. The reaction mixture was stirred for 30 minutes at –23° C. for 30 minutes followed by at room temperature for 1 hr. The mesolate formed in this reaction was short lived and produced almost instantaneously the elimination product. The mixture was poured on to ethyl acetate (200 mL) and was washed with water, 10% aqueous citric acid, water, aqueous sodiumbicarbonate and finally with water. The organic layer was dried over sodium sulfate, evaporated under reduced pressure and chromatographed over a silica gel column. Elution with 5 to 20% ethyl acetate in hexane afforded 528 mg of pure product as a gum. $^1$H NMR (CDCl$_3$): 0.80 (3H, d, J=6.6 Hz), 0.84 (3H, d, J=6.6 Hz), 1.43 (1H, ddd, J=13.8, 9.0, 5.1 Hz), 1.62 (1H, ddd, J=13.8, 10.2, 5.4 Hz), 1.81 (1H, m), 3.59 (3H, s), 3.70 (1H, dd, J=10.2, 5.4 Hz), 3.78 (3H, s), 3.88 (3H, s), 3.93 (2H, ABq, J=13.8 Hz), 4.80 (2H, ABq, J=7.2 Hz), 6.84 (2H, d, J=8.7 Hz), 6.98 (2H, d, J=8.7 Hz), 7.15 (2H, d, J=8.4 Hz), 7.54 (1H, s), 7.99 (2H, d, J=9.0 Hz); $^{13}$C NMR (CDCl$_3$): 21.33, 23.00, 24.78, 42.25, 55.26, 55.37, 58.04, 58.65, 60.04, 100.82, 114.17 (2C), 114.24 (2C), 126.46, 127.75, 130.67 (2C), 131.04, 132.06, 133.00, 159.55, 160.98, 161.56, 170.23; FABMS (m/z): 475 (M+Li).

c. Synthesis of 1-(N-hydroxy-methoxymethyl)-3-(2-methyl-propyl)-5-(p-methoxybenz-1-enyl)-2,6-diketopiperazin-3,4-ene

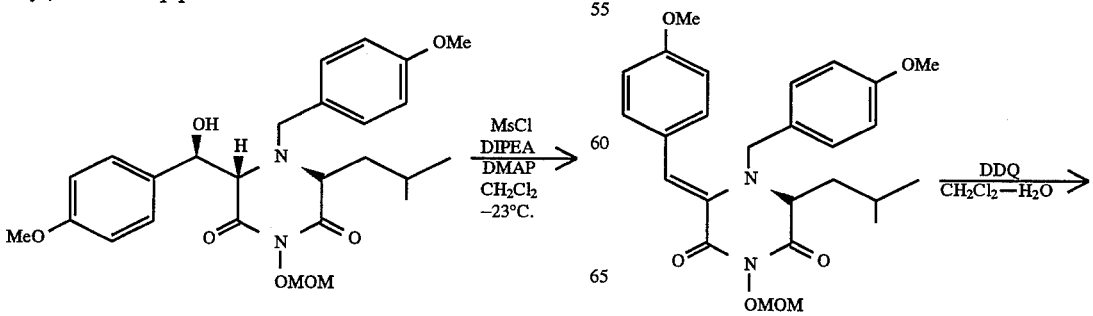

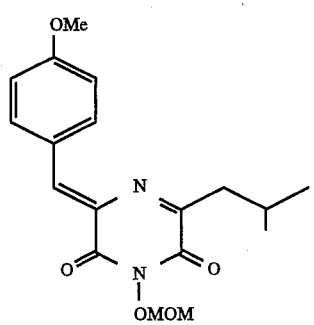

PMB derivative (235 mg) was reacted in methylene chloride (10 mL) and water (5 mL) with 3 equivalent of DDQ in an identical condition for overnight. The reaction mixture was filtered and then diluted with 200 mL of methylene chloride and washed with water, 10% aqueous sodium bicarbonate, water, dried (Na$_2$SO$_4$), evaporated under reduced pressure and chromatographed over a silica gel column. Elution with 10% ethyl acetate in hexane yielded 45 mg of the target compound as a solid. $^1$H NMR (CDCl$_3$): 1.04 (6H, d, J=6.9 Hz), 2.26 (1H, nonet, J=6.9 Hz), 2.73 (2H, d, J=6.9 Hz), 3.68 (3H, s), 3.88 (3H, s), 5.12 (2H, s), 6.96 (2H, d, J=9.0 Hz), 7.78 (1H, s), 8.20 (2H, d, J=8.4 Hz); FABMS (m/z): 353 (M+Li).

d. Synthesis of 1-(N-hydroxy)-3-(2-methyl-propyl)-5-(Z-p-methoxybenz-1-enyl)-2,6-diketopiperazine-3,4-ene

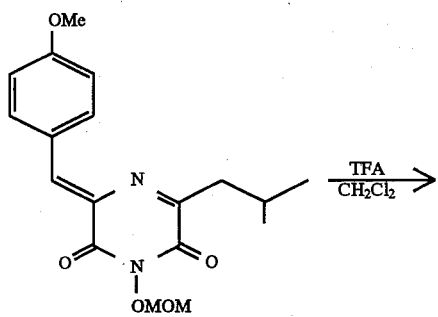

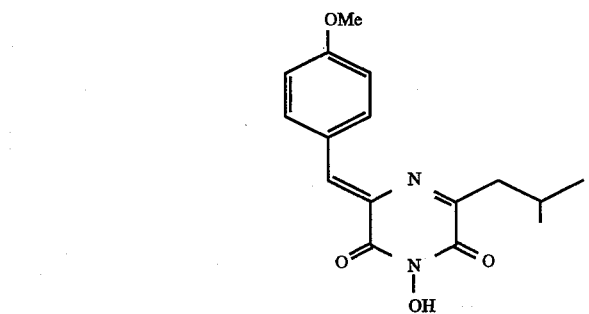

Trifluoroacetic acid (0.3 mL) was added to a cooled (0° C.) solution of MOM ether (25 mg) in methylene chloride (1.0 mL) and the solution was stirred 30 minutes under nitrogen followed by additional stirring overnight at room temperature. The solvents were removed under a stream of nitrogen and the residue was triturated with acetonitrile and filtered to give 5 mg of product as a solid. The filtrate was chromatographed on a Zorbax RX C-8 (9.4×250 mm) column and eluted with 50% aqueous acetonitrile at a flow rate of 4 mL per minute to give an additional 4 mg of the product. $^1$H NMR (CDCl$_3$): 1.05 (6H, d, J=6.6 Hz), 2.30 (1H, nonet, J=6.6 Hz), 2.77 (2H, d, J=7.2 Hz), 3.91 (3H, s), 6.99 (2H, d, J=9.3 Hz), 7.86 (1H, s), 8.27 (2H, d, J=8.7 Hz); FABMS (m/z): 315 (M+2Li-H).

EXAMPLE 13 a. Synthesis of 1-(N-hydroxy-methoxymethyl)-3-(benzyl)-4-(N-paramethoxybenzyl)-5-(1-hydroxy-2-methyl-propyl)-2,6-diketopiperazine

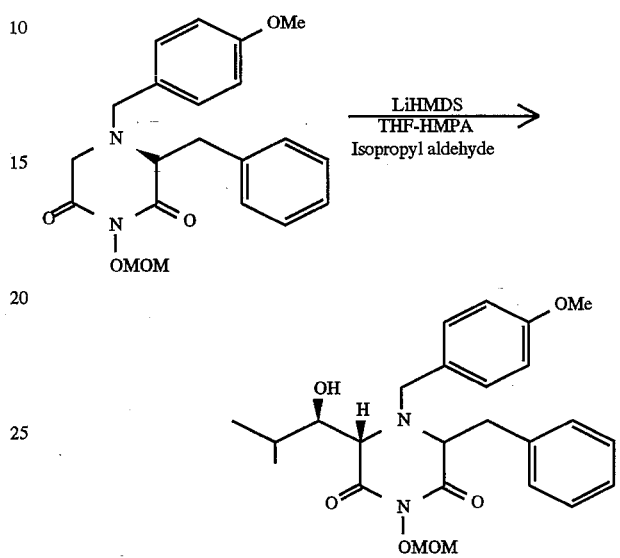

Aldol condensation of MOM ether (2.7 g, 7 mmol) using 3 equivalent of isopropylaldehyde after chromatography gave a ~2:1 mixture of β/α-hydroxy compound (1.8 g) as a gum which was used for the elimination reaction.

b. Synthesis of 1-(N-hydroxy-methoxymethyl)-3-(benzyl)-4-(N-paramethoxybenzyl)-5-(2-methyl-E and Z-prop-1-enyl)-2,6-diketopiperazine

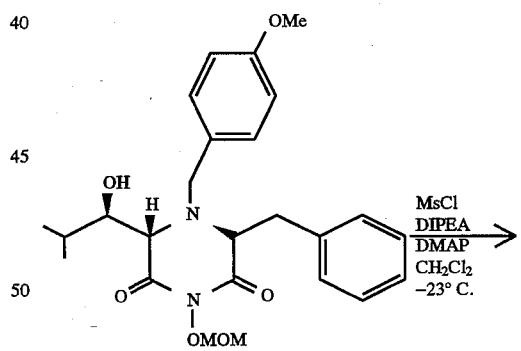

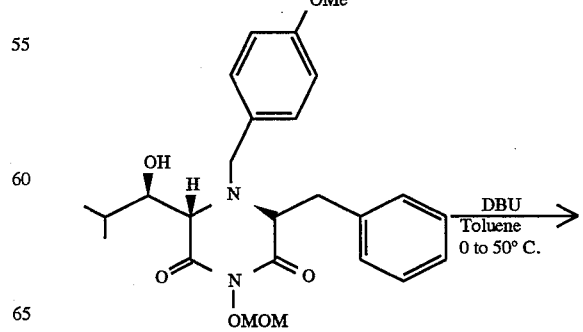

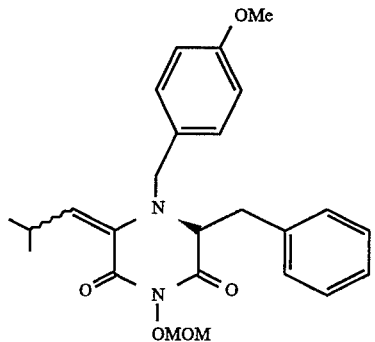

Mesylation of hydroxy compound (1.6 g, 3.5 mmol) followed by elimination using DBU and chromatography on silica gel gave the Z-isomer (810 mg). $^1$H NMR (CDCl$_3$): 0.99 (3H, d, J=6.9 Hz), 1.09 (3H, d, J=6.6 Hz), 2.74 (1H, dd, J=13.8, 10.8 Hz), 2.88 (1H, m), 2.98 (1H, dd, J=13.8, 4.5 Hz), 3.63 (3H, s), 3.78 (3H, s), 3.78 (1H, dd, J=masked due to overlap), 3.80 (2H, ABq, J=13.8 Hz), 4.96 (2H, ABq, J=7.5 Hz), 6.72 (2H, d, J=8.7 Hz), 6.73 (1H, d, J=10.8 Hz), 6.88 (2H, d, J=8.4 Hz), 7.01 (2H, m), 7.25 (3H, m); $^{13}$C NMR (CDCl$_3$): 21.49, 22.15, 26.71, 38.77, 55.29, 58.22, 61.01, 63.19, 100.78, 113.96 (2C), 126.81,127.95, 128.23 (2C), 129.16 (2C), 129.87 (2C), 132.67, 146.45, 159.27, 160.78, 169.62.

c. Synthesis of 1-(N-hydroxy-methoxymethyl)-3-(benzyl)-5-(2-methyl- Z-prop-1-enyl)-2,6-diketopiperazine-3,4-ene

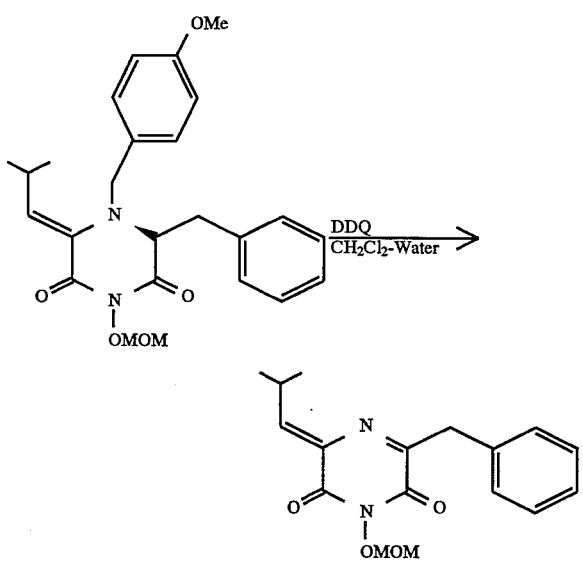

DDQ reaction of Z-olefin (660 mg) and purification on silica gel gave the desired imine (40 mg) as an oil and the diketoimide (65 mg) as a semi solid. $^1$H NMR (CDCl$_3$): 1.12 (6H, d, J=6.9 Hz), 3.50 (1H, m), 3.64 (3H, s), 4.06 (2H, s), 5.06 (2H, s), 7.15 (1H, d, J=9.9 Hz), 7.24–7.36 (5H, m); $^{13}$C NMR (CDCl$_3$): 21.79 (2C), 27.45, 39.75, 58.40, 100.62, 126.93, 128.53, 129.54, 133.99, 135.72, 154.96, 156.39, 159.34, 159.65.

EXAMPLE 14 a. Synthesis of 1-(N-hydroxy-methoxymethyl)-3-(benzyl)-4-(N-paramethoybenzyl)-5-(1-hydroxy-p-methoxybenzyl)-2,6-diketopiperazine

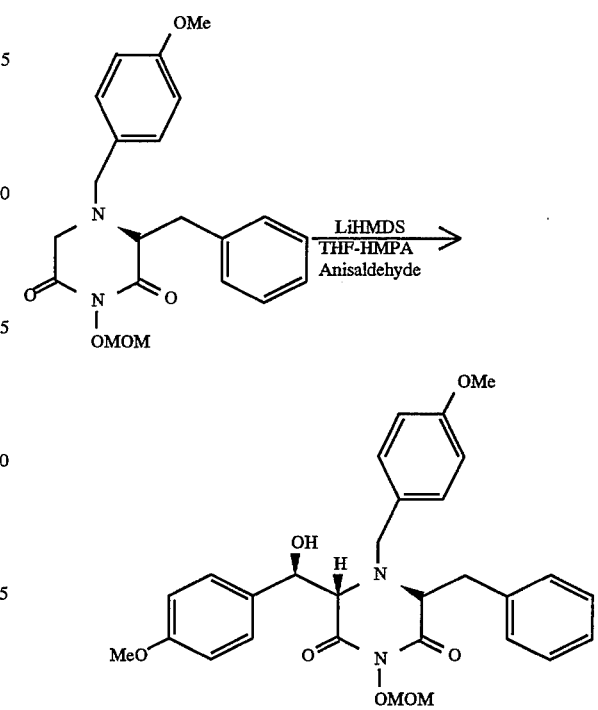

Reaction of MOM ether (2.5 g, 6.5 mmol) with p-methoxybenzaldehyde (2 eq) after chromatography gave the β-hydroxy product (1.2 g) as a gum. $^1$H NMR (CDCl$_3$): 2.94 (1H, dd, J=14.7, 10.5 Hz), 3.16 (1H, dd, J=14.4, 4.2 Hz), 3.27 (1H, d, J=12.9 Hz), 3.67 (3H, s), 3.74 (3H, s), 3.76 (1H, d, J=12.9 Hz), 3.84 (3H, s), 3.86 (1H, dd, J=10.8, 4.5 Hz), 3.97 (d, J=13.2 Hz), 4.01 (1H, d, J=7.5 Hz), 5.08 (2H, ABq, J=7.5 Hz), 5.14 (1H, brd, J=7.5 Hz), 6.43 (2H, d, J=8.7 Hz), 6.56 (2H, d, J=9.0 Hz), 6.79 (2H, d, J=8.7 Hz), 6.8 (2H, d, J=8.1 Hz), 7.07–7.22 (5H, m); $^{13}$C NMR (CDCl$_3$): 34.10, 52.00, 55.23, 55.38, 58.45, 63.08, 64.86, 71.91,100.85, 113.67 (2C), 113.85 (2C), 126.61, 127.29, 128.25 (2C), 128.29 (2C), 129.25 (2C), 130.00 (2C), 131.44, 136.54, 159.04, 159.62, 168.97, 169.76.

b. Synthesis of 1-(N-hydroxy-methoxymethyl)-3-(benzyl)-4-(N-para-methoxybenzyl)-5-(Z-p-methoxybenz-1-enyl)-2,6-diketopiperazine

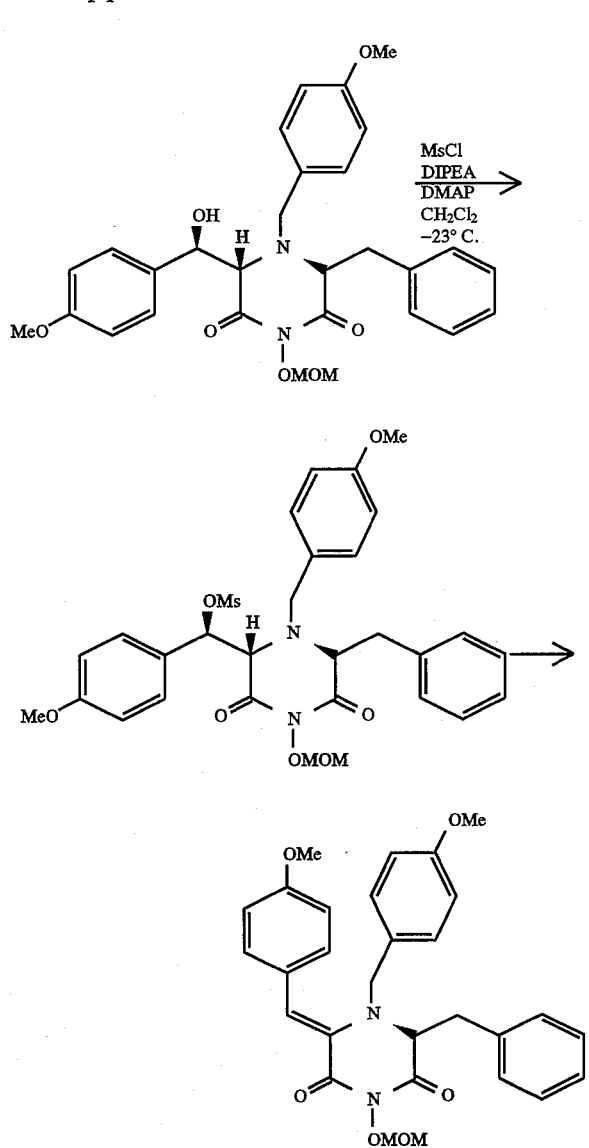

This reaction was performed identical to other aromatic analogs with the hydroxy compound (2.0 g, 3.85 mmol) reacted with methane sulfonyl chloride to afford after silica gel chromatography the Z-olefin (1.32 g) as a gum. $^1$H NMR (CDCl$_3$): 2.83 (1H, dd, J=14.1, 11.4 Hz), 3.12 (1H, dd, J=13.8, 3.9 Hz), 3.61 (3H, s), 3.72 (1H, d, J=13.8 Hz), 3.77 (3H, s), 3.83 (3H, s), 3.87 (1H, d, J=14.1 Hz), 4.00 (1H, dd, J=10.8, 3.9 Hz), 4.83 (2H, ABq, J=7.2 Hz), 6.77 (2H, d, J=8.7 Hz), 6.78 (2H, d, J=9.0 Hz), 6.93 (2H, d, J=8.7 Hz), 7.03 (1H, dd, J=7.5, 1.2 Hz), 7.18=7.24 (5H, m), 7.54 (1H, s), 7.59 (2H, d, J=8.7 Hz); $^{13}$C NMR (CDCl$_3$): 39.46, 55.26, 55.37, 58.08, 58.61, 63.50, 100.86, 113.90 (2C), 114.11 (2C), 126.10, 126.90, 127.68, 128.45 (2C), 129.52 (2C), 130.19 (2C), 130.34, 131.65, 133.39 (2C), 136.69, 159.46, 160.86, 161.51, 169.27; FABMS (m/z): 475 [M+Li].

c. Synthesis of 1-(N-hydroxy-methoxymethyl)-3-(benzyl)-5-(p-methoxy-benz-1-enyl)-2,6-diketopiperazin-3,4-ene

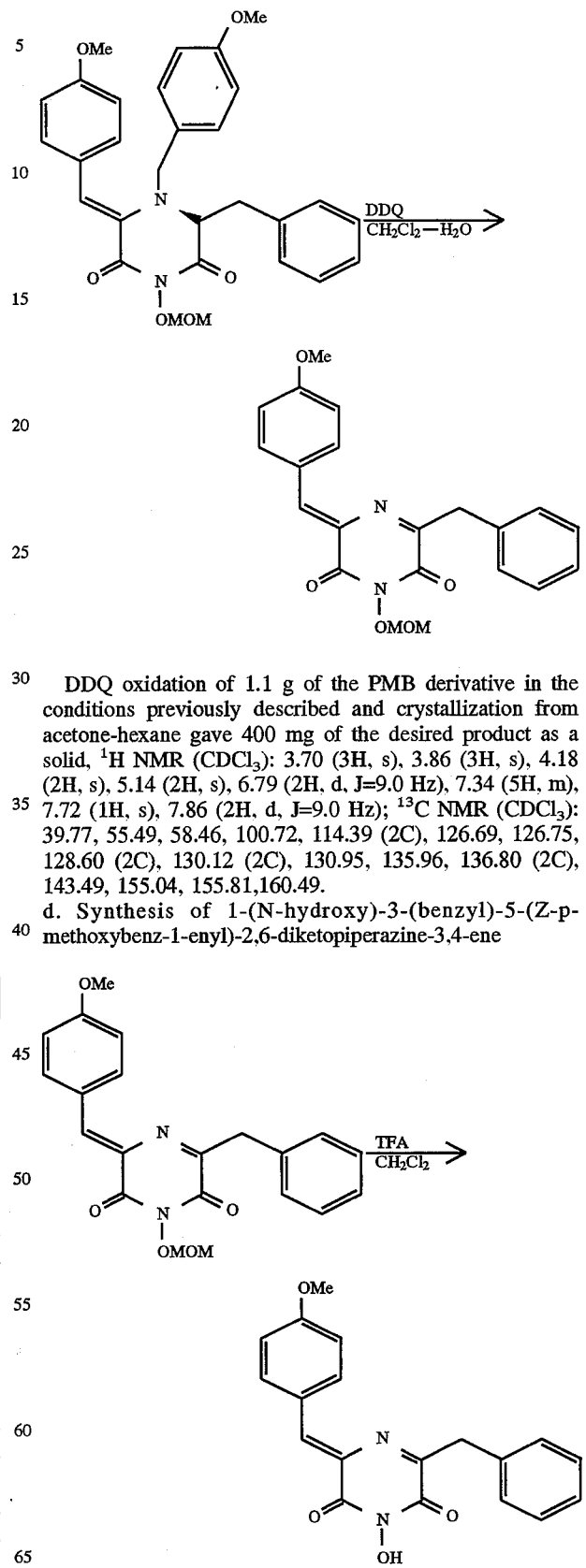

DDQ oxidation of 1.1 g of the PMB derivative in the conditions previously described and crystallization from acetone-hexane gave 400 mg of the desired product as a solid, $^1$H NMR (CDCl$_3$): 3.70 (3H, s), 3.86 (3H, s), 4.18 (2H, s), 5.14 (2H, s), 6.79 (2H, d, J=9.0 Hz), 7.34 (5H, m), 7.72 (1H, s), 7.86 (2H, d, J=9.0 Hz); $^{13}$C NMR (CDCl$_3$): 39.77, 55.49, 58.46, 100.72, 114.39 (2C), 126.69, 126.75, 128.60 (2C), 130.12 (2C), 130.95, 135.96, 136.80 (2C), 143.49, 155.04, 155.81, 160.49.

d. Synthesis of 1-(N-hydroxy)-3-(benzyl)-5-(Z-p-methoxybenz-1-enyl)-2,6-diketopiperazine-3,4-ene Deprotection of the MOM group from the MOM ether (60 mg) with TFA followed by Prep HPC on A Zorbax RX C-8 (22×250 mm) column and elution with 50% aqueous acetonitrile at a flow rate of 10 mL per minute gave 15 mg of pure product as a powder. $^1$H NMR (CDCl$_3$): 3.89 (3H, s), 4.12 (2H, s), 6.83 (2H, d, J=9.3 Hz), 7.36 (5H, m), 7.81 (1H, s), 7.95 (2H, d, J=9.0 Hz).

EXAMPLE 15 a. Synthesis of 1-(N-hydroxy-methoxymethyl)-3-(benzyl)-4-(N-paramethoxybenzyl)-5-(1-hydroxy-p-fluoro-benzyl)-2,6-diketopiperazine

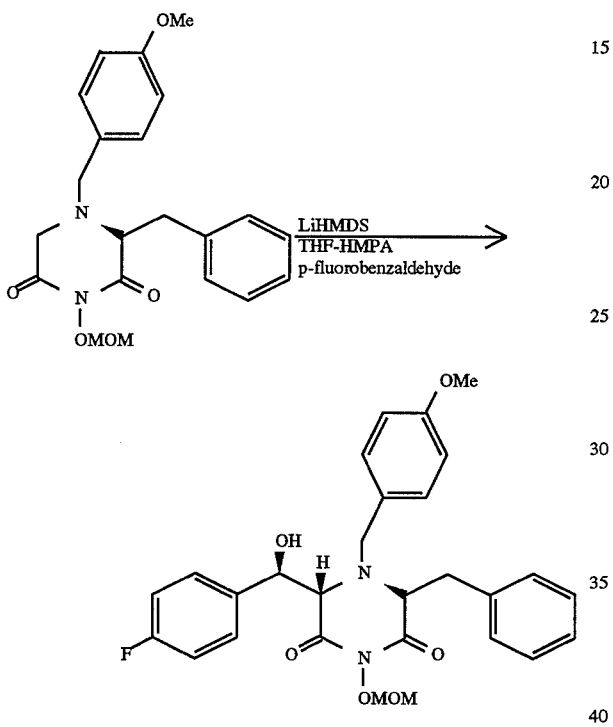

Reaction of MOM ether (1.9 g, 4.95 mmol) with p-fluorobenzaldehyde (1.5 eq) after chromatography gave the β-hydroxy product (1.62 g) as a foam which tamed into a gum. $^1$H NMR (CDCl$_3$): 2.94 (1H, dd, J=14.7, 10.8 Hz), 3.20 (1H, dd, J=15.0, 4.5 Hz), 3.28 (1H, d, J=13.2 Hz), 3.67 (3H, s), 3.74 (3H, s), 3.89 (1H, dd, J=10.8, 4.5 Hz), 3.956 (1H, d, J=7.8 Hz), 3.957 (1H, d, J=13.2 Hz), 5.08 (2H, ABq, J=7.2 Hz), 5.13 (1H, dd, J=7.8, 1.8 Hz), 6.41 (2H, d, J=8.4 Hz), 6.57 (2H, d, J=8.7 Hz), 6.84 (2H, dd, J=6.9, 1.5 Hz), 6.91 (2H, dd, J=8.4, 5.4 Hz), 7.23 (3H, m); $^{13}$C NMR (CDCl$_3$): 33.97, 51.97, 55.24, 58.47, 63.11, 64.86, 71.58, 100.87, 113.73 (2C), 115.24 (2C, d, J=25.7 Hz), 126.77, 127.05, 128.35 (2C), 128.87 (2C, d, J=9.8 Hz), 129.16 (2C), 129.91 (2C), 135.14 (d, J=3.9 Hz), 136.49, 159.10, 162.60 (d, J=294.4 Hz), 168.82, 169.62.

b. Synthesis of 1-(N-hydroxy-methoxymethyl)-3-(benzyl)-4-(N-paramethoxybenzyl)-5-(Z-p-fluoro-benz-1-enyl)-2,6-diketopiperazine

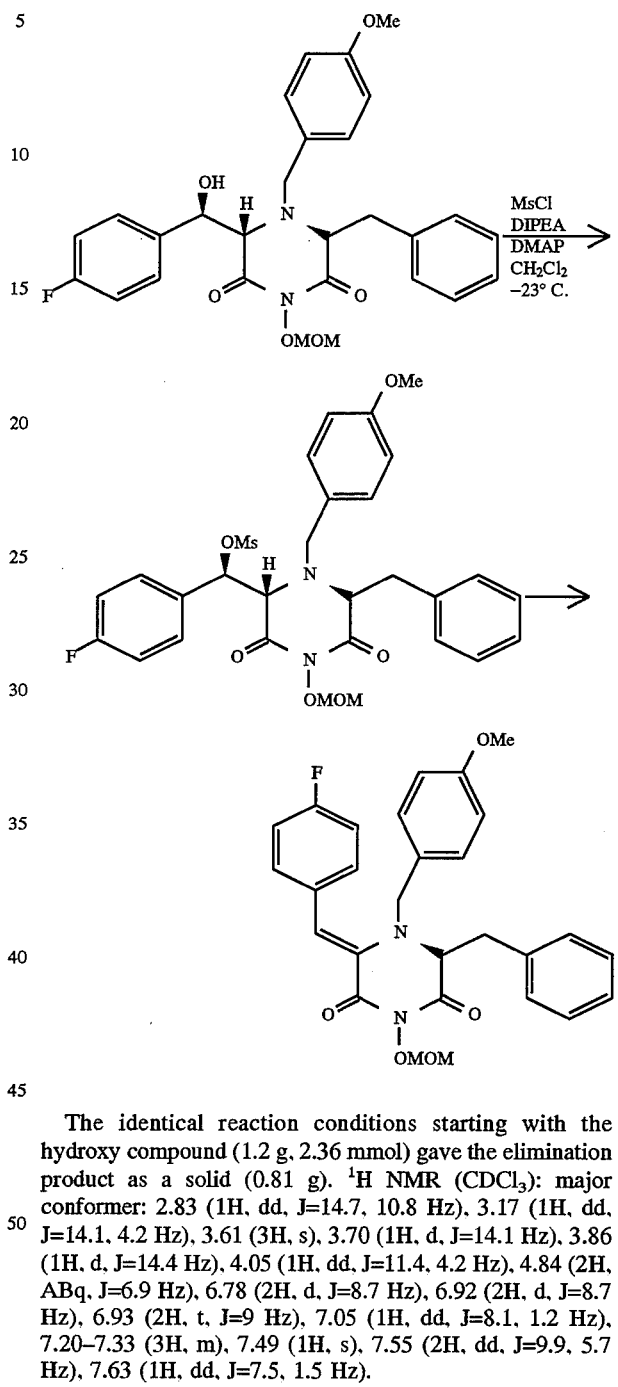

The identical reaction conditions starting with the hydroxy compound (1.2 g, 2.36 mmol) gave the elimination product as a solid (0.81 g). $^1$H NMR (CDCl$_3$): major conformer: 2.83 (1H, dd, J=14.7, 10.8 Hz), 3.17 (1H, dd, J=14.1, 4.2 Hz), 3.61 (3H, s), 3.70 (1H, d, J=14.1 Hz), 3.86 (1H, d, J=14.4 Hz), 4.05 (1H, dd, J=11.4, 4.2 Hz), 4.84 (2H, ABq, J=6.9 Hz), 6.78 (2H, d, J=8.7 Hz), 6.92 (2H, d, J=8.7 Hz), 6.93 (2H, t, J=9 Hz), 7.05 (1H, dd, J=8.1, 1.2 Hz), 7.20–7.33 (3H, m), 7.49 (1H, s), 7.55 (2H, dd, J=9.9, 5.7 Hz), 7.63 (1H, dd, J=7.5, 1.5 Hz).

c. Synthesis of 1-(N-hydroxy-methoxymethyl)-3-(benzyl)-5-(Z-p-fluoro-benz-1-enyl)-2,6,-diketopiperazin-3,4-ene

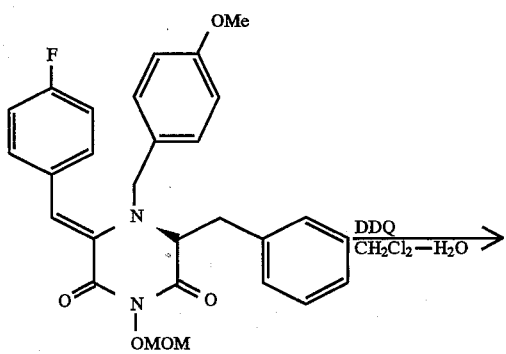

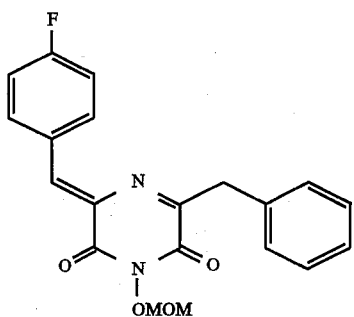

DDQ oxidation of protected compound (0.70 g, 1.43 mmol) followed by trituration by acetone-hexane gave imine product (150 mg) as a powder, $^1$H NMR (CDCl$_3$): 3.69 (3H, s), 4.20 (2H, s), 5.13 (2H, s), 6.94 (2H, t, J=9.0 Hz), 7.27–7.43 (5H, m), 7.70 (1H, s), 7.85 (2H, dd, J=9,0, 5.7 Hz).

d. Synthesis of 1-(N-hydroxy)-3-(benzyl)-5-(Z-p-fluoro-benz-1-enyl)-2,6-diketopiperazine-3,4-ene

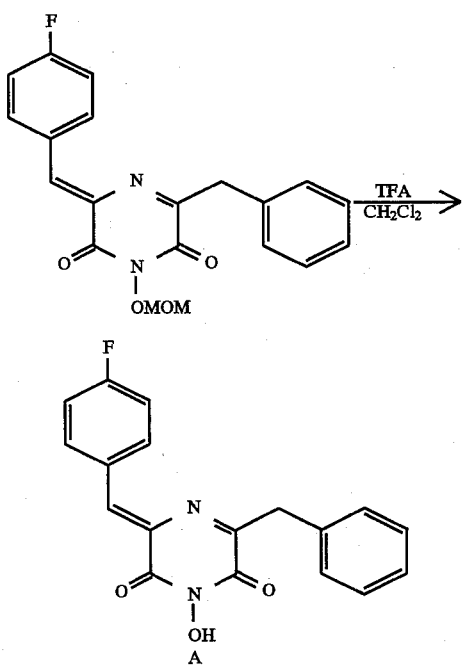

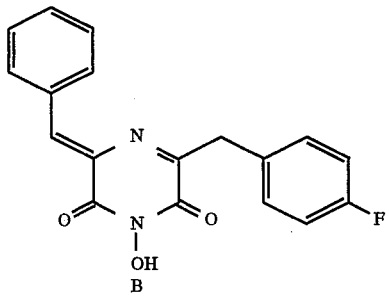

Deprotection of the MOM group of the MOM ether (50 mg) under the conditions described above gave two isomeric products A and B. After completion of the reaction the products were purified on a Zorbax RX C-8 analytical HPLC column (45% aqueous acetonitrile containing 0.1% TFA at a flow rate of 1 mL/min) in multiple runs. The fractions were quickly freeze dried and then the identical fractions were combined to give 4 mg of product B ($t_R$=13.7 min) and 4 mg of product A ($t_R$=14.7 min) as amorphous solids. A: $^1$H NMR (CDCl$_3$): 4.23 (2H, s), 6.98 (2H, t, J=8.8 Hz), 7.32–7.40 (5 Hz, m), 7.79 (1H, s), 7.93 (2H, dd, J=8.8, 5.6 Hz); CIMS (m/z): 325 [M+H]. B: $^1$H NMR (CDCl$_3$): 4.20 (2H, s), 7.07 (2H, t, J=8.8 Hz), 7.31 (2H, dd, J=8.4, 5.2 Hz), 7.36 (2H, t, J=7.6 Hz), 7.48 (1H, tt, J=7.6, 1.2 Hz), 7.86 (1H, s), 7.94 (2H, dd, J=7.6, 1.2 Hz); CIMS (m/z): 325 [M+H].

EXAMPLE 16

Synthesis of Tetrahydro compound

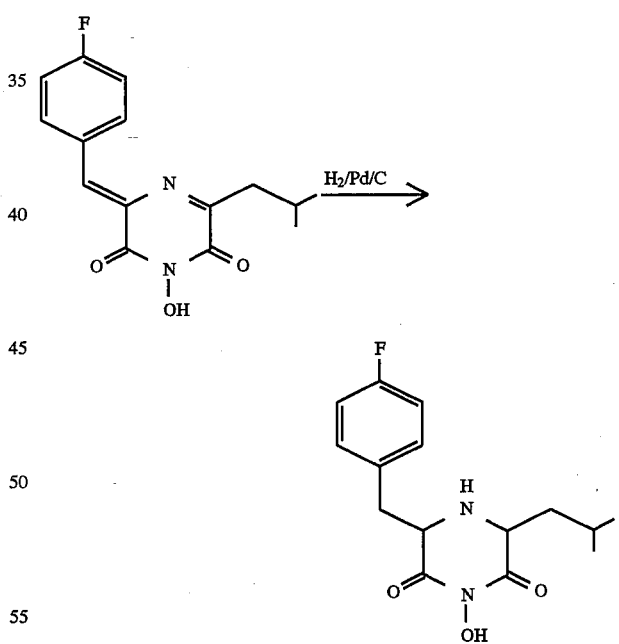

To a solution of the imine (6.6 mg) in ethyl acetate (1 mL) and methanol (0.2 mL) was added 10% palladium over charcoal (5 mg) and the mixture was evacuated and flushed with hydrogen. The evacuation and flush cycle was repeated three times and was finally connected to a balloon filled with hydrogen. The starting material was consumed within 20 minutes (HPLC, Zorbax RX C-8, 50% aq. acetonitrile, 1 mL per min.) and a single product was formed. The catalyst was removed by filtration and solvents were evaporated under reduced pressure to give a gum which was triturated with methylene chloride-hexane to give 6.1 mg of a solid. $^1$H NMR (CDCl$_3$): 0.86 (3H, d, J=6.3 Hz), 0.91 (3H, d, J=6.6 Hz), 1.46 (1H, ddd, J=14.1, 9.0, 5.1 Hz), 1.74 (1H, m), 1.96 (1H, ddd, J=13.5, 9.3, 2.6 Hz), 3.15 (1H, dd, J=14.4, 7.5 Hz), 3.36 (1H, dd, J=14.4, 4.2 Hz), 3.57 (1H, dd, J=9.0, 3.6 Hz), 3.82 (1H, dd, J=7.2, 4.5 Hz), 7.02 (2H, t, J=8.7 Hz), 7.23 (2H, dr, J=8.7, 5.7 Hz), $^{13}$C NMR (CDCl$_3$): 21.39, 23.11, 24.55, 35.40, 39.32, 57.26, 59.68, 115.80 (2C, d, J=25.3 Hz), 131.12 (2C, d, J=10 Hz), 131.55 (d, J=3.5 Hz), 162.11 (d, J=294.3 Hz), 167.45, 168.98; ESIMS (m/z): 295 [M+H], 589 (2M+H].

The following examples illustrates representative compositions containing the compounds of the invention.

EXAMPLE A 1000 hard gelatin capsules, each containing 500 milligrams of Compound I are prepared from the following formulation:

| Compound | Grams |
| --- | --- |
| Compound of Example 9 | 500 |
| Starch | 750 |
| Dibasic calcium phosphate hydrous | 5000 |
| Calcium stearate | 2.5 |

The finely powered ingredients are mixed well and granulated with 10 percent starch paste. The granulation is dried and compressed into tablets.

EXAMPLE B 1000 hard gelatin capsules, each containing 500 milligrams of Compound I are prepared from the following formulation:

| Compound | Grams |
| --- | --- |
| Compound of Example 9 | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE C 250 milliliters of an injectable suspension are prepared by conventional procedures having the following formulation:

| 5% DMSO/water | 250 milliliters |
| --- | --- |
| Compound of Example 9 | 400 milligrams |

The ingredients are blended and thereafter sterilized for use.

EXAMPLE D

An ointment suitable for topical application may be prepared by intimately dispersing 13 milligrams of Compound I in 1 gram of commercially available polyethylene/ hydrocarbon gel.

EXAMPLE E

An aerosol composition may be prepared having the following formulation:

| | Per Canister |
| --- | --- |
| Compound of Example 9 | 24 mg |
| Lecithin NF, liquid concentrate | 1.2 mg |
| Trichlorofluoromethane | 4.025 g |
| Dichlorodefluoromethane | 12.15 g |

While the preferred embodiments of the invention have been described herein in detail, numerous alternative embodiments are contemplated as falling within the scope of the claims.

What is claimed is:

1. A compound of the formula (II)

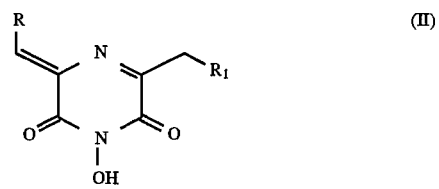

wherein:

R is $C_1$–$C_6$ alkyl, phenyl, naphthyl, substituted phenyl, wherein the substituents are selected from halogen, $C_1$–$C_6$ alkoxy or aryloxy; the term "aryl" in aryloxy meaning phenyl, naphthyl, substituted phenyl, $R_1$ is $C_1$–$C_6$ alkyl, phenyl, naphthyl, substituted phenyl, wherein the substituents are selected from halogen, $C_1$–$C_6$ alkoxy or aryloxy; the term "aryl" in aryloxy meaning phenyl, naphthyl, substituted phenyl, or a pharmaceutically acceptable salt thereof.

2. A compound as claimed in claim 1 which is 1-(N-hydroxy)-3-(2-methyl-propyl)-5-(Z-benz-1-enyl)-2,6-diketopiperazine-3,4-ene, 1-(N-hydroxy)-3-(2-methyl-propyl)-5-(Z-p-fluoro-benz-1-enyl)-2,6-diketopiperazine-3,4-ene, 1-(N-hydroxy)-3-(2-methyl-propyl)-5-(Z-o-fluoro-benz-1-enyl)-2,6-diketopiperazine-3,4-ene, 1-(N-hydroxy)-3-(2-methyl-propyl)-5-(Z-m-fluoro-benz-1-enyl)-2,6-diketopiperazine-3,4-ene, 1-(N-hydroxy)-3-(2-methyl-propyl)-5-(Z-p-methoxy-benz-1-enyl)-2,6-diketopiperazine-3,4-ene, 1-(N-hydroxy)-3-(benzyl)-5-(Z-p-methoxybenz-1-enyl)-2,6-diketopiperazine-3,4-ene, or 1-(N-hydroxy)-3-(benzyl)-5-(Z-p-fluoro-benz-1-enyl)-2,6-diketopiperazine-3,4-ene.

3. A compound of the formula (III)

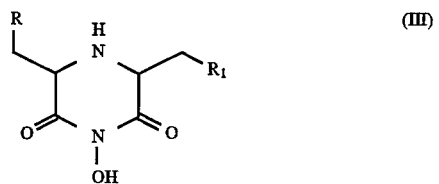

wherein:

R is $C_1$–$C_6$ alkyl, phenyl, naphthyl, substituted phenyl, wherein the substituents are selected from halogen, $C_1$–$C_6$ alkoxy or aryloxy; the term "aryl" in aryloxy meaning phenyl, naphthyl, substituted phenyl, $R_1$ is $C_1$–$C_6$ alkyl, phenyl, naphthyl, substituted phenyl, wherein the substituents are selected from halogen, $C_1$–$C_6$ alkoxy or aryloxy; the term "aryl" in aryloxy meaning phenyl, naphthyl, substituted phenyl, or a pharmaceutically acceptable salt thereof.

4. A pharmaceutical composition which comprises an effective amount of a compound as defined in claim 1 and a pharmaceutically acceptable carrier therefor.

5. A composition as defined in claim 4 wherein the compound of claim 1 is present in an amount of at least 1% by weight.

6. A method of inhibiting influenza virus mRNA transcription in a host cell containing capped and methylated mRNA primers which comprises administering to said host cell an effective amount of a compound of claim 1 for inhibiting the viral use of said capped and methylated primer.

* * * * *